(12) United States Patent
Domanico et al.

(10) Patent No.: US 7,863,050 B2
(45) Date of Patent: Jan. 4, 2011

(54) METHODS AND COMPOSITIONS FOR PURIFICATION OF NUCLEIC ACID FROM A HOST CELL

(75) Inventors: Michael J. Domanico, Longmont, CO (US); Matt Myers, Boulder, CO (US); Kristian Keane, Boulder, CO (US); Lisa R. Braun, Denver, CO (US); Thomas Kolzau, Hamburg (DE)

(73) Assignee: Qiagen North American Holdings, Inc., Valencia, CA (US)

( * ) Notice: Subject to any disclaimer, the term of this patent is extended or adjusted under 35 U.S.C. 154(b) by 0 days.

(21) Appl. No.: 12/358,128

(22) Filed: Jan. 22, 2009

(65) Prior Publication Data

US 2009/0246859 A1 Oct. 1, 2009

Related U.S. Application Data

(62) Division of application No. 10/387,646, filed on Mar. 12, 2003, now abandoned.

(51) Int. Cl.
  *C12N 1/08* (2006.01)
  *G01N 1/18* (2006.01)
(52) U.S. Cl. .......................... 436/94; 436/63; 436/174; 436/175; 436/177; 436/178; 435/6; 435/29; 435/270; 536/25.4
(58) Field of Classification Search .................. 436/63, 436/94, 174, 175, 177, 178; 435/4, 6, 29, 435/270; 536/25.4
See application file for complete search history.

(56) References Cited

U.S. PATENT DOCUMENTS

| | | | | |
|---|---|---|---|---|
| 4,652,517 A | * | 3/1987 | Scholl et al. | 435/5 |
| 5,128,247 A | * | 7/1992 | Koller | 435/91.53 |
| 6,545,144 B2 | * | 4/2003 | Kolzau et al. | 536/25.4 |
| 6,548,256 B2 | * | 4/2003 | Lienau et al. | 435/6 |
| 6,586,585 B1 | * | 7/2003 | Bastian | 536/25.4 |
| 7,670,768 B1 | * | 3/2010 | Heath et al. | 435/6 |
| 2002/0012982 A1 | * | 1/2002 | Blakesley et al. | 435/183 |
| 2003/0073830 A1 | * | 4/2003 | Heath et al. | 536/25.4 |
| 2003/0134412 A1 | * | 7/2003 | Kolzau et al. | 435/320.1 |
| 2003/0166916 A1 | * | 9/2003 | Kolzau et al. | 536/25.4 |
| 2003/0191302 A1 | * | 10/2003 | Kolzau et al. | 536/25.4 |
| 2004/0157219 A1 | * | 8/2004 | Lou et al. | 435/6 |
| 2009/0068724 A1 | * | 3/2009 | Deggerdal et al. | 435/270 |

FOREIGN PATENT DOCUMENTS

| | | | |
|---|---|---|---|
| WO | 02/074954 | * | 9/2002 |

* cited by examiner

*Primary Examiner*—Maureen M Wallenhorst
(74) *Attorney, Agent, or Firm*—Todd Lorenz; Arnold & Porter LLP

(57) ABSTRACT

Methods and compositions are provided for gently lysing and solubilizing cells. Methods and compositions are further provided for quickly purifying high quality low molecular weight nucleic acid from host cells. Target cells are treated with a pre-chilled lysis solution having a zwitterionic detergent, for example n-Dodecyl-N,N-dimethyl-3-ammonio-1-propanesulfonate, and a brief room-temperature incubation. Where nucleic acid purification is required, the lysis solution-treated cells are contacted with a nucleic acid capture matrix having an average pore size of at least about 1 μm.

21 Claims, 14 Drawing Sheets

METHODS AND COMPOSITIONS FOR PURIFICATION OF NUCLEIC ACID FROM A HOST CELL

CROSS-REFERENCE TO RELATED APPLICATIONS

This application claims priority to and is a divisional of U.S. Patent application Ser. No. 10/387,646, filed Mar. 12, 2003 (now abandoned), the disclosure of which is incorporated herein by reference in its entirety.

FIELD OF THE INVENTION

The invention generally relates to methods and compositions for isolating nucleic acid from cellular sources. More specifically, the invention relates to methods and compositions for directly isolating low molecular weight nucleic acid, for example, extrachromosomal DNA, from a crude cell lysate using an efficient one step lysis composition in conjunction with a nucleic acid capture matrix.

BACKGROUND OF THE INVENTION

The ability to isolate low molecular weight nucleic acid, and extrachromosomal nucleic acid in particular, from a host cell is often requisite to a large number of protocols used in molecular biology, as well as a basic requirement in a number of downstream uses in biotechnology and clinical research. For example, typical cloning protocols anticipate the availability of plasmid vector DNA for the transformation of target cells. The quality, i.e., level of purity and integrity, of the extrachromosomal nucleic acid is often determinative of the success of the cloning procedure, and as such, is a critical parameter for the entire procedure. Further, DNA sequencing, restriction digestion reactions and subsequent ligation reactions, are generally dependent on the quality of the starting DNA material. As such, there has been, and continues to be, a need for reliable methods for purifying high quality low molecular weight nucleic acid from host cells.

Conventional low molecular weight nucleic acid purification schemes often progress in more or less two stages: in the first stage, host cells harboring the target nucleic acid, i.e. extrachromosomal nucleic acid, are gently lysed and the contents solubilized; and in the second stage, the target nucleic acid is separated from the contaminating protein, RNA, high molecular weight nucleic acid (i.e. chromosomal DNA), and other macromolecules via one of several commonly used chemical or enzymatic methods. In general, conventional target nucleic acid purification schemes have proven to be either labor intensive and time consuming, yet yielding a high quality product, or relatively fast and labor efficient, but yielding a relatively low quality product.

More particularly, one of the more commonly used time efficient methods for isolating target nucleic acid involves an alkaline lysis technique. The alkaline lysis method typically incorporates a NaOH/SDS lysis solution in sequential combination with a potassium acetate solution, and centrifugation steps to preferentially release and separate the target nucleic acid from other contaminating materials. A separate centrifugation or filtration step is used to produce a cleared lysate. Alcohol precipitation of the cleared lysate is necessary to precipitate the nucleic acid. Although the alkaline lysis method is fairly rapid, it takes approximately 30 to 45 minutes, and the purity of the resultant nucleic acid is fair, i.e., useful in restriction digestions and other more basic detection type procedures, it does not provide quality extrachromosomal nucleic acid.

In a further approach, the cleared lysate as prepared by the alkaline lysis procedure can be combined with a chaotropic substance, for example guanidinium salt, urea and sodium iodide, in the presence of a DNA-binding solid phase (e.g. beads or other binding matrix) to purify the target nucleic acid. The nucleic acid is bound to the solid phase in a one-step reaction, washed to remove residual contaminants and the nucleic acid is then eluted in low salt buffer. Although methods combining alkaline lysis with the chaotropic bind/wash/elute steps can provide higher quality nucleic acid, they are still time-consuming, taking approximately twenty-five minutes, and require more handing.

As such, there is a continuing need in the art for a simple and time efficient method, and corresponding solutions, for purifying a low molecular weight target nucleic acid such as extrachromosomal DNA from host cells, and in particular, for methods and solutions for purifying plasmid DNA from host cells. Against this backdrop the present invention has been developed.

SUMMARY OF THE INVENTION

The present invention provides a one-step method for lysing and isolating low molecular weight nucleic acid from host cells, using a single solution and a nucleic acid capture matrix. In a preferred embodiment, the lysis solution is pre-chilled to enhance nucleic acid purity. In a further preferred embodiment, the nucleic acid capture matrix comprises a capture matrix material having a pore size of at least 1 µm. In contrast to prior art protocols, low molecular weight nucleic acid can be isolated quickly (approximately 8 to 10 minutes) and easily (few reagents required) following the methods described herein at high yield and purity.

Preferably, the low molecular weight nucleic acid isolated following the methods and compositions of the invention has a $A_{260/280}$ ratio of from about 1.7 to 1.9, and has minimal protein contamination as determined by visual, i.e. photometric, detection methods, i.e., standard gel electrophoresis and like methods. More preferably, low molecular weight nucleic acid isolated using the methods and compositions of the invention can typically be sequenced for at least 600 bases, i.e., having a 600 quality score (q)$\geq$20 per sample (Codon-Code software, PHRED Interphace) (PHRED q$\geq$20 score of 600).

One embodiment of the present invention provides a lysis composition for purifying low molecular weight nucleic acid from host cells. The lysis composition preferably comprises a buffering agent and a detergent. In a particularly preferred embodiment, the detergent comprises a non-ionic detergent or a zwitterionic detergent, for example, n-Decyl-N,N-dimethyl-3-ammonio-1-propanesulfonate. In additional embodiments, the lysis composition further comprises a salt, polyethylene glycol, lysozyme, and/or RNase.

In a further preferred embodiment, the lysis solution is pre-chilled prior to its addition to host cells.

In another embodiment of the invention a kit is provided for purifying low molecular weight nucleic acid from host cells. Preferably, the kit includes a nucleic acid capture matrix and a lysis composition comprising a buffering agent, a non-ionic or zwitterionic detergent, and optionally a salt, polyethylene glycol, lysozyme and/or RNase. In a particularly preferred embodiment, the nucleic acid capture matrix comprises a capture matrix material incorporated into a spin column having an average pore size of at least about 1 µm, and more preferably at least about 3 µm.

Another embodiment of the present invention is a method for purifying low molecular weight nucleic acid from host cells. The method includes the steps of adding a lysis composition to the host cells, wherein the lysis composition comprises from 0.2% to 6% zwitterionic or non-ionic detergent and is preferably pre-chilled prior to use, combining the released low molecular weight nucleic acid with a nucleic acid capture matrix, and eluting the captured low molecular weight nucleic acid into a capture tube. In alternative embodiments, the lysis composition is incubated on the host cells at room temperature for at least 2 minutes, and more preferably at least 3 minutes prior to the addition to the nucleic acid capture matrix.

Additionally, the methods and compositions of the present invention can also be modified, as described in greater detail below, for the preferential isolation of solubilized protein, RNA, BACs, and high molecular weight nucleic acid. In these further embodiments, a lysis solution comprising a buffer and zwitterionic detergent are employed in conjunction with the appropriate ingredient for high yield and quality purification of the target macromolecule, for example RNase, lysozyme, or DNase.

These and various other features as well as advantages which characterize the invention will be apparent from a reading of the following detailed description and a review of the appended claims.

BRIEF DESCRIPTION OF THE DRAWINGS

FIG. 7A shows lysis method DNA (labeled on the gel as FastPlasmid DNA) compared to QIAgen prepared DNA. FIG. 7B graphically compares concentration from lysis method prepared DNA of the present invention to DNA prepared via QIAgen, Invitrogen, BioRad and Promega.

DETAILED DESCRIPTION OF THE INVENTION

Definitions

Figure 1A:
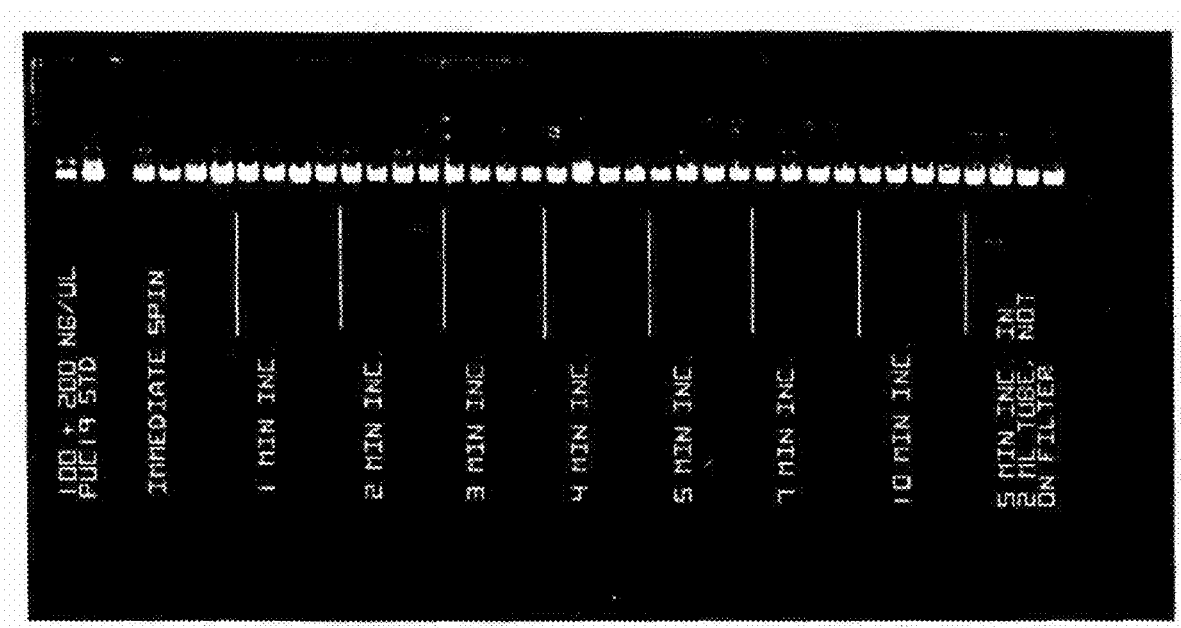
FIGS. 1A and 1B illustrate isolated plasmid DNA as visualized on a stained 0.5% agarose gel (1A) and graphically (1B) where the cells were incubated with Lysis solution for various amounts of time at room temperature. The graph illustrates both concentration and $A_{212}$ absorbance readings for each condition.

The following definitions are provided to facilitate understanding of certain terms used herein and are not meant to limit the scope of the present disclosure.

"$A_{260/280}$" refers to a commonly used nucleic acid quantitation technique where the sample to be tested is measured for absorption at approximately 260 nm and 280 nm. The ratio of absorbance at 260 to 280 is used as an indicator of nucleic acid purity. Protein contaminants tend to lower the ratio below about a ratio of 1.6 and RNA contaminants tend to raise the ratio to above 1.9-2.0.

"$A_{212}$" refers to a single absorbance reading used to aid in the detection of protein contamination in a nucleic acid-containing sample. For example, a sample having a high $A_{212}$ reading likely has some level of protein contamination in the sample, which when combined with the $A_{260/280}$ ratio and gel agarose analysis is indicative of the sample's quality. A reading of 10 is considered high for purposes of the present invention.

"Host cell" refers to cells containing a target nucleic acid molecule, for example a heterologous nucleic acid molecule such as a plasmid or other low molecular weight nucleic acid, in which case the host cell is typically suitable for replicating the nucleic acid molecule of interest. Examples of suitable host cells useful in the present invention include, bacterial, yeast, insect and mammalian cells. Specific examples of such cells include, SF9 insect cells, (Summers and Smith, 1987, Texas Agriculture Experiment Station Bulletin, 1555), Chinese Hamster Ovary (CHO) cells (Puck et al., 1958, Proc Natl Acad Sci USA 60:1275-1281), *E. Coli* DH5α cells, as well as various other bacterial cell sources, for example the *E. Coli* strains: DH10b cells, XL1Blue cells, XL2Blue cells, Top10 cells, HB101 cells, and DH12S cells.

As used herein, "nucleic acid" or "NA" refers to both a deoxyribonucleic acid and a ribonucleic acid. As used herein, "nucleic acid sequence" refers to the order or sequence of deoxyribonucleotides or ribonucleotides along a strand. They may be natural or artificial sequences, and in particular genomic DNA (gDNA), complementary DNA (cDNA), messenger RNA (mRNA), transfer RNA (tRNA), ribosomal RNA (rRNA), hybrid sequences or synthetic or semisynthetic sequences, oligonucleotides which are modified or otherwise. These nucleic acids may be of human, animal, plant, bacterial or viral origin and the like. They may be obtained by any technique known to persons skilled in the art, and in particular by the screening of libraries, by chemical synthesis or by mixed methods including the chemical or enzymatic modification of sequences obtained by the screening of libraries. They may be chemically modified, e.g. they may be pseudonucleic acids (PNA), oligonucleotides modified by various chemical bonds (for example phosphorothioate or methyl phosphonate), or alternatively oligonucleotides which are functionalized, e.g. which are coupled with one or more molecules having distinct characteristic properties.

In the case of deoxyribonucleic acids, they may be single- or double-stranded, as well as short oligonucleotides or longer sequences. In particular, the nucleic acids advantageously consist of plasmids, vectors, episomes, expression cassettes and the like. These deoxyribonucleic acids may carry genes of therapeutic interest, sequences for regulating transcription or replication, anti-sense sequences which are modified or otherwise, regions for binding to other cellular components, and the like. "Low molecular weight nucleic acid" as used herein refers to heterologous extrachromosomal pieces of nucleic acid, for example plasmids, having a base length of approximately 2 kb to 20 kb, and in some aspects from 2 kb to 8 kb. In a preferred embodiment, the low molecular weight nucleic acid of the invention comprises a plasmid, where the plasmid has an origin of replication or replicator, a selectable marker and a cloning site. In some instances the low molecular weight nucleic acid is supercoiled. Example plasmids useful in the invention include pUC19, pUC18, pBS2, pEGFP, pBR322, and the like. In addition, low molecular weight nucleic acid is envisioned to encompass other forms of nucleic acid, for example, RNA.

"High quality nucleic acid" as used herein generally refers to nucleic acid associated with a sufficiently low level of contaminants such that it can be digested by appropriate restriction endonuclease enzymes and can be used directly in conventional transformation and transfection procedures, i.e., no further substantial processing of the nucleic acid is required. Preferably, such high quality nucleic acid has a $A_{260/280}$ ratio of from about 1.6 to 2.0 and more preferably from about 1.7 to 1.9. Alternatively and/or additionally, such high quality nucleic acid can be sequenced for up to at least 400 bases using standard sequencing techniques, and more preferably for up to 600 bases, typically having a PHRED score $q \geq 20$.

"Isolated" and "purified" for purposes of the present invention are interchangeable, and refer to a polynucleotide, for example low molecular weight nucleic acid, that has been separated from cellular debris, for example, high molecular weight DNA, RNA and protein. This would include an isolated RNA sample that would be separated from cellular debris, including DNA.

"Nucleic acid capture matrix" refers to a media or material used for capturing the low molecular weight nucleic acid of the present invention, including, e.g., capture matrix materials typically composed of silica, nylon, carboxy, and the like as well as silica-based beads, including silica-coated magnetized beads. Typically, the capture matrix material of the present invention comprises fiber filters having a pore size of greater than 1 μm, and more typically greater than or equal to 3 μm. The nucleic acid capture matrix or "NA capture matrix" of the present invention may further comprise one or more distinct layers of capture matrix material for capture of the low molecular weight nucleic acid. It should be noted that where multiple layers of matrix material are used, the materials need not be the same in or between each layer of material. In particularly preferred embodiments, the NA Capture Matrix is supported by a frit and incorporated into a conventional spin column or similar device.

"PHRED" or "PHRED score" refers to a software program used to measure DNA sequence quality. The software is purchased from CodonCode Corporation, version 0.020425.c. For purposes of the present invention, a PHRED q20 score of 600 is equivalent to approximately 730 bases at >98.5% accuracy.

"Polyethylene glycols" or "PEGs" useful in the present invention are commercially available diols having a molecular weight of from 2,000 to 10,000 daltons, and more preferably about 8,000 daltons. The use of PEG having other molecular weight constraints, for example higher than 10,000 daltons, is also contemplated for use in the compositions and methods of the present invention, although perhaps not as effective at providing a high yield/quality product.

"Detergent" as used herein refers to any amphiphilic molecule having the property of being inserted into biological membranes and destabilizing them. This results from the capacity of detergent molecules to rupture the membranes by becoming inserted into the phospholipid double layers and by solubilizing the lipids and the proteins (La Cellule, Ed. Vigot and Decarie, 1988, pp. 581-583).

"Zwitterionic" detergent refers to detergents exhibiting zwitterionic character, including for example sulfobetaines sold under the brand names Zwittergent™ and Anzergent™. Particularly suitable detergents are the following: N-dodecyl-N,N-dimethylammonio-3-propane sulfate or the corresponding N-tetradecyl or N-hexadecyl compound (type "Zwittergent": Zwittergent 3-14, 3-16), N-dodecyl-N,N-dimethylglycine (Empigen BB.RTM.), aminoxide, CHAPS, CHAPSO and .alpha.-lecithin (.alpha.-phosphatidylcholin) or .alpha.-lysolecithin (.alpha.-lysophosphatidylcholin).

The invention provides methods and compositions for lysing and solubilizing host cells. In particular, the invention provides a simple three to five minute procedure that utilizes a single solution for lysing and releasing the contents of a cell and contemporaneously solubilizing the majority of the cell's protein. Embodiments of the present invention include methods and solutions for the preferential isolation of low molecular weight nucleic acid, e.g., extrachromosomal DNA, RNA, or other regions of DNA from the host cell, as well as the preferential separation of protein from nucleic acid from a host cell.

In one preferred embodiment, methods and compositions are provided for purifying low molecular weight nucleic acid, for example plasmid DNA, from target host cells. In particular, plasmid DNA is purified from host bacterial cells at high yields and at a quality useful in cloning procedures, restriction digest reactions, and in sequencing reactions. The methods of the invention utilize a single solution to lyse the bacterial cells and bind nucleic acid. Low molecular weight nucleic acid is released from host cells and captured on a nucleic acid capture matrix directly from the crude lysate. The matrix is washed with an appropriate wash buffer and eluted in a final end-use condition. The entire procedure can be performed in less than 10 minutes and in preferred embodiments can be performed in approximately 8 or fewer minutes.

Lysis Solutions:

The invention is based upon, among other things, a lysis solution comprising a buffering ingredient and a detergent. In preferred embodiments, the detergent is a zwitterionic detergent, and in particular a detergent selected from the group that includes, but is not limited to, n-Tetradecyl-N,N-dimethyl-3-ammonio-1-propanesulfonate, n-Octyl-N,N-dimethyl-3-ammonio-1-propanesulfonate, n-Decyl-N,N-dimethyl-3-ammonio-1-propanesulfonate, n-Dodecyl-N,N-dimethyl-3-ammonio-1-propanesulfonate, and the like. Note that other zwitterionic detergents are envisioned to be within the scope of the present invention, especially those zwitterionic detergents that have like properties to the enumerated zwitterionic detergents above. Embodiments of this solution are capable of lysing target host cells and solubilizing a majority of the cellular protein. In further preferred embodiments, the lysis solution of the present invention can be used in conjunction with other nucleic acid isolation methods, for example a high concentration of chaotropic salt, to drive the binding of nucleic acid to a solid support matrix. Preferred buffer/detergent embodiments of the solution include lysozyme and either DNase or RNase.

In additional embodiments, it is also contemplated that the above-described lysis solution may further comprise a chelating agent, a salt, polyethylene glycol, lysozyme, and RNase or DNase. As will be appreciated by those of skill in the art, the RNase, for removal of RNA in a DNA purification procedure, or DNase, for removal of DNA in a RNA purification procedure, are technically not required to purify the target nucleic acid using the methods of the present invention, but nucleic acid yield and purity are improved significantly by inclusion of these ingredients. Further, the inclusion of lysozyme has a significant impact on resultant yields, and is particularly preferred as an additional ingredient of the lysis solution of the present invention. Inclusion of these components are contemplated for use in nucleic isolation methods in accordance with the present invention.

In a preferred embodiment, the buffer component of the lysis solution is Tris-Cl having a pH of approximately 8, although other buffering compounds are contemplated. Typically, the final concentration of Tris-Cl in the lysis solution is from about 0 to about 200 mM, and preferably from about 15 to 75 mM. Note that the buffering component of the solution can be modified so that little or no pH modification of the final solution is required. For example, the buffer component can be a combination of Tris-amino and Tris-amino hydrochloride to provide a final lysis solution pH of approximately 7.9 to 8.4. One illustrative combination is to include approximately 17 mM Tris amino with 28 mM Tris amino hydrochloride in the final lysis solution. Other buffering combinations can be used to obtain the appropriate lysis solution pH, which as mentioned above, is optimally from 7.9 to 8.4.

The preferred salt for use in the lysis solution is any common salt used in nucleic acid precipitation, for example, NaCl, $NH_4Cl$, $NH_4SO_4$, $MgCl_2$, and the like. In preferred embodiments, the salt is NaCl, due partly to its availability and relative low cost. Final concentrations of salt in the lysis solution preferably range from 200 to 800 mM and more preferably about 400 mM.

The preferred chelating agent for use in the lysis solution is EDTA, but it is contemplated that EGTA can also be used. Final concentrations of EDTA of from 0 to 20 mM, and preferably about 9 mM, are useful in embodiments of the present invention.

The preferred molecular weight of polyethylene glycol (PEG) for use in the present invention is about 2,000 to 10,000 daltons, and more preferably about 8,000 daltons. Typically, final PEG concentration in the lysis solution is from 2 to 20% and preferably from 2 to 8%. Note that PEG is prepared by using techniques well known in the art, for example by heating to an appropriate temperature and filtering to remove particulates. Surprisingly, PEG having higher molecular weight may have deleterious effects on the quality of the purified low molecular weight nucleic acid of the present invention.

Typically, embodiments of the lysis solution include lysozyme, for example egg white lysozyme or recombinant lysozyme, at a final concentration of from approximately 300 to 2,000 µg/ml, and preferably from 800 to 1,200 µg/ml. In addition, RNase (or DNase where the purification target is RNA), for example RNase A, RNase 1, RNase TI, is preferably included in the Lysis solution at a concentration of from 200 to 400 µg/ml. In both cases, the lysozyme or RNase is stored as a lyophilized powder or in solution. For example, RNase is typically stored in a 100 mM NaCl, 10 mM Tris, and 1 mM EDTA solution. Note that the lysozyme and RNase are required for optimized yield, i.e., full release of the nucleic acid, and removal of RNA contaminants, respectively, and can be included at higher concentrations than disclosed above, but with limited enhancement in yield and quality. Lysozyme, RNase and DNase are commercially available.

The lysis solution also includes a detergent at a final concentration of from about 0.2% to 6%, and preferably from about 2 to 4%. Note that lower amounts of detergent can be used in the solutions of the present invention, especially where the concentration of cells being lysed and solubilized is low. Further, although higher levels of detergent are contemplated for use in the present invention, they may not add additional functional value and thus are less preferred.

Typically, the detergent is either an ionic detergent, non-ionic detergent, or a zwitterionic detergent. Typical ionic detergents for use in the present invention include, but are not limited to Deoxycholic Acid. Typical non-ionic detergents for use in the present invention include, but are not limited to, Triton X-100, Apo 10, Apo 12 and NP40. Typical zwitterionic detergents include, but are not limited to, CHAPS and sulfobetaines, the sulfobetaine detergents sold under the brand name Zwittergent™ and Anzergent™, for example. Note also that in some cases a non-detergent zwitterionic material can also be used, but is not preferred.

In preferred embodiments of the present invention the detergent is a Zwitterionic detergent, for example, sold under the brand names Zwittergent™ and Anzergent™, having the chemical names of: n-Tetradecyl-N,N-dimethyl-3-ammonio-1-propanesulfonate, n-Octyl-N,N-dimethyl-3-ammonio-1-propanesulfonate, n-Decyl-N,N-dimethyl-3-ammonio-1-propanesulfonate, and n-Dodecyl-N,N-dimethyl-3-ammonio-1-propanesulfonate. One preferable detergent for use in the present invention is n-Decyl-N,N-dimethyl-3-ammonio-1-propanesulfonate. Note that detergents of the present invention can be purchased under the brand names, for example, of: Anzergent 3-14, Analytical Grade; Anzergent 3-8, Analytical Grade; Anzergent 3-10, Analytical Grade; Anzergent 3-12, Analytical Grade, respectively or zwittergent 3-8, zwittergent 3-10, zwittergent 3-12 and zwittergent 3-14, CHAPS, CHAPSO, Apo10 and Apo12.

Note that it is also envisioned that compatible detergents for use in the present invention can be mixed together to provide the requisite detergent composition (final concentration) for use in the lysis solution. For example, a detergent having a final concentration of 2% in the lysis solution can be composed of a 50:50 mixture of n-Decyl-N,N-dimethyl-3-ammonio-1-propanesulfonate:n-Dodecyl-N,N-dimethyl-3-ammonio-1-propanesulfonate.

Further, it is envisioned that other constituents can be included in embodiments of the lysis solution, for example, a chaotropic salt at concentrations of between 50 mM and 6M, and preferably between 200 mM and 400 mM, can be included in the solution to assist in the denaturation of proteins. Further, an alcohol, like isopropanol, may be included in the solution at concentrations of between 0.5% to 25%, to assist in the precipitation of the low molecular weight nucleic acid.

During the preparation of the lysis solution, the lysozyme, RNase (or DNase), and detergent should be added after the other components of the solution have been brought to a pH of from 7.9 and 8.4, and preferably to a pH of about 8.1. Where modification of the pH is necessary, any number of well known acids or bases in the art, for example, HCl or NaOH, can be used.

Note also that as discussed above, the pH of the lysis solution should be fairly close to the acceptable range by preparing the solution with the appropriate amounts and compositions of buffering solutions.

The lysis solution is preferably stored at 4° C., although it is envisioned that storage can also be at room temperature. Typically, solutions can be stored for up to 3 months. However, it is also envisioned that the lysis solution in the absence of RNase, DNase, and lysozyme can be stored for up to one to two years. The lysozyme, RNase and DNase may be advantageously added at the time of use from a concentrated solution or as noted above from a lyophilized powder when longer storage times are required.

In a particularly preferred embodiment, the lysis solution is added to target host cells at a temperature of from about 0° C. to 10° C., more preferably 1° C. to 8° C., most preferably 0° C. to 4° C., generally in the range of about 2° C. to 6° C. As used herein, the term "pre-chilled" as used herein refers to the lysis composition of the present invention within the foregoing temperature ranges. As such, when a lysis procedure is anticipated, the lysis solution should be placed on ice for a sufficient period of time prior to use with the host cells to achieve the requisite temperature.

Table 1 provides an illustrative lysis solution for use in the methods of the present invention.

TABLE 1

Illustrative Lysis Solution

| Ingredient | Preferred Ingr. | Final Conc. | Units |
|---|---|---|---|
| Buffer | Tris-Cl (pH 8) | 45 | mM |
| Chelating agent | EDTA | 9 | mM |
| Salt | NaCl | 400 | mM |
| PEG | MW 8000 | 8 | % |
| RNase | RNase A | 305 | μg/ml |
| Lysozyme | Egg White Lysozyme | 1000 | μg/ml |
| Detergent | n-Decyl-N,N-dimethyl-3-ammonio-1-propanesulfonate | 3 | % |

Lysis and Solubilization Method

The methods of the present invention are used to lyse and solubilize target host cells using embodiments of the above-described lysis solution. For purposes of lysing and solubilizing the target cells, the lysis solution comprises a buffering agent and a detergent, preferably a zwitterionic detergent. In particularly preferred embodiments, the lysis solution further comprises lysozyme. The lysis solution can also include other optional constituents as described above, dependent on the anticipated use of the lysed and solubilized material. For example, where isolation of RNA is anticipated, inclusion of DNase is advantageous, or where isolation of a DNA plasmid vector is anticipated, the lysis solution may include RNase.

In a preferred embodiment, the method comprises vortexing or mixing the cells with a pre-chilled lysis solution for a period of from 10 to 30 seconds, followed by a one to ten minute, and more preferably three to five minute, room temperature incubation. This preferred method of the invention provides a compatible procedure to an alkaline lysis procedure, taking less than half the time and generally providing a higher quality product, i.e., cleared lysate.

Lysis Method and Nucleic Acid Purification

The methods of the present invention further include performing a one-solution purification procedure on host cells that harbor target low molecular weight nucleic acid molecules. The procedure results in the isolation of the low-molecular weight nucleic acid, for example plasmid DNA, directly from the lysed cells, i.e., directly from the crude cell lysate. Typically, using the methods and compositions of the present invention, the low molecular weight nucleic acid is released from the host cells, and a substantial majority of the host cellular protein is solubilized by the composition embodiments of the present invention. The released low-molecular weight nucleic acid is captured from the crude cell lysate by a nucleic acid capture matrix, and washed on that matrix in an alcohol-based buffer. The resultant captured low molecular weight nucleic acid is eluted from the capture matrix in an appropriate buffer, typically at a high yield and excellent quality. As such, following the methods of the present invention a single buffer is utilized to lyse the host cell and bind/capture the target low-molecular weight nucleic acid on a solid support, i.e., the nucleic acid capture matrix. The entire process, as more fully described below, can be performed in approximately eight to ten minutes, and requires only standard laboratory equipment.

In more detail, bacterial or other appropriate host cells are transformed with target low molecular weight nucleic acid, as is well known in the art. The host cells are grown to a target concentration (typically $5 \times 10^8$ to $20 \times 10^8$ cells/ml or $A_{600}$ of between 1 and 4 OD units), harvested, and spun down, as is also well known in the art. The LB growth media (or any other solution on the cells) is decanted off of the cell pellet, and pre-chilled lysis solution (0° C. to 4° C.) of the present invention added to the cell pellet. Typically, approximately 400 μl of lysis solution is added for each 1.5 ml of culture material, although this may be modified to optimize for cell concentration and lysis solution compositions, for example, a lower concentration of detergent can be included in the lysis solution where a smaller number of cells is being treated. Note that in an alternative embodiment of the present invention, the lysis solution is added directed to the cell culture, i.e., prior to the cells being spun down and growth media decanted off of the cell pellet. Typically, a ratio of about 2:1 to about 1:3 cells:lysis solution is combined, the ratio dependent on the cell concentration, embodiment of the lysis solution and other like parameters. Although addition of the lysis solution directly to the cells removes the centrifugation step required for removal of the growth media, it may result in slightly increased protein contamination of the isolated nucleic acid during the lysis purification method, due to the higher levels of potentially contaminating material in the starting material. Nevertheless, where such contaminants are of less concern or time is of the essence the present invention enables a further reduction in the requisite handlings steps.

The lysis solution, the composition of which is discussed in greater detail below, is continuously vortexed or mixed on the host cells for approximately 10 to 30 seconds, and more preferably for about 20 seconds. The re-suspended cell mixture is next incubated at room temperature for a period of from one to ten minutes, and more preferably from three to five minutes, and most preferably about five minutes. The room temperature incubation results in the substantial release of the low-molecular weight nucleic acid from the host cells and the solubilization of a substantial portion of the host cellular protein. Note, shorter lysis solution room temperature incubations can be used in conjunction with the present invention, although the yield of low molecular weight nucleic acid is correspondingly lower. In addition, longer room temperature lysis incubations may be used, but little improvement in low molecular weight nucleic acid yield or quality is typically observed beyond the five to ten minute incubation.

The inclusion of the pre-chilled lysis buffer on the host cells, and subsequent room temperature incubation, provides a temperature gradient during which host cell proteins are solubilized by the lysis buffer. Without being bound by theory, it is believed that this aspect of the present method takes advantage of different cellular proteins solubility over a range of temperatures (from 0° C.-4° C. to room temperature) and to some extend pH changes (due to the temperature change of the buffer). However, it is envisioned that lysis buffer temperature and host cell incubation temperature can be modified in relation to the methods of the present invention, with some effect on the overall yields and purity of low molecular weight nucleic acid.

After the room temperature incubation, the released low molecular weight nucleic acid and solubilized cellular debris is transferred to a spin column having at least one layer of nucleic acid (NA) capture matrix (preferred embodiments can have a second and/or third layer of NA capture matrix incorporated into the spin column). The above mixture is spun through the spin device at approximately 14,000 RPM (20,000×G) for approximately 30 seconds using a mini- or microcentrifuge (one of skill in the art will recognize that other speeds and times can be used in the context of the present invention as long as the fluid is pulled through the spin column, as is well known in the art). Note that other procedures can be used in this aspect as well, for example vacuum filtering and the like of the material through the nucleic acid capture matrix.

In an alternative embodiment, NA capture matrix material is included directly in the lysis buffer and added directly to the host cells during the room temperature lysis buffer/host cell incubation. In such cases, the lysis buffer/nucleic acid capture matrix must be thoroughly mixed before addition to the host cell pellet so that the matrix is thoroughly re-suspended.

The NA capture matrix binds a portion of the released low molecular weight nucleic acid from the cellular debris, i.e., crude lysate. Surprisingly, nucleic acid capture matrix with a pore size of greater than 1-2 µm is preferred for use in the invention, and preferably, multiple layers of nucleic acid capture matrix, each having pore sizes of at least 1-2 µm is used during capture of the low molecular weight nucleic acid. Note that matrix materials having pore sizes of less than 1-2 µm are also envisioned for use in the present invention, but display a tendency to become clogged and require additional processing not necessary with the larger pore materials. In addition, the larger pore materials preferred for use herein tend to provide superior capture characteristics in conjunction with the invention not present in smaller pore materials In order to maximize the purity of the captured low molecular weight nucleic acid, one or more wash steps is performed on the loaded nucleic acid capture matrix. The wash buffer is typically a 20 mM Tris-Cl, pH of 7.2, 0.2 M NaCl, and 2 mM EDTA, pH of 8.0)/isopropanol solution. Typically, the ratio of Tris buffer:Isopropanol is about 30-35: 70-65, and is preferably about 32.5:67.5 (note that other like alcohols can be used in place of isopropanol, for example ethanol). Note that other wash buffer compositions can be used with the present invention as long as they preferentially dissociate contaminants to low molecular weight nucleic acid from the capture matrix. The wash step removes loosely associated protein and other macromolecules from the loaded nucleic acid capture matrix.

Finally, the low-molecular weight nucleic acid is eluted from the NA capture matrix using a 10 mM Tris, 0.1 mM EDTA solution, having a pH of approximately 8.5. Typical elution parameters include using smaller volumes to maintain a higher concentration of the target low molecular weigh nucleic acid, and minimizing the amount of EDTA or other enzyme inhibitory constituents in the elution buffer.

As illustrated with the above elution buffer, elution of the low molecular weight nucleic acid can be performed in a solution compatible with the end-use application, for example, using an elution buffer having little inhibitory activity on polymerase enzymes. As such, the end-use application can be performed directly on the eluted sample without having to precipitate and re-suspend the nucleic acid in the appropriate buffer. Other elution buffer solutions for use in the present invention include water, TE buffer, 10-50 mM Tris buffer, and the like.

Nucleic Acid Capture Matrix:

A number of different nucleic acid capture matrix compositions are useful in conjunction with the methods and compositions of the present invention for capture of low molecular weight nucleic acid. Capture matrix compositions for use in the present invention include silica-, nylon-, and acrylic-based materials. Typical pore sizes for the filter capture matrix material are from 1 to 25 µm, and preferably from 1 to 5 µm, and most preferably from 3 to 5 µm. It is noted that matrix materials having larger pore sizes can be used in conjunction with the present invention, but are likely less effective in capturing low molecular weight nucleic acid. In addition, smaller pore size capture matrix materials, i.e., smaller than 1 µm, can also be used in conjunction with the present invention, but tend to clog during the capture process (note that matrix materials having pore sizes of between 1 and 2 µm can also show some level of clogging, dependent on the number of matrix layers and size of sample).

In preferred embodiments, a first layer of capture matrix material is incorporated into a spin device as is well known in the art. The capture matrix material will be of a composition and pore size compatible with the parameters previously described, but is preferably a glass fiber having a pore size of between 3 to 5 µm. In some embodiments, the spin device includes two layers of capture matrix material, for example, a first (top) layer of material having a pore size of approximately 5 µm and a second layer (lower) of capture matrix material having a pore size of approximately 3 µm. The additional capture matrix material provides an additional surface area/support for the capture of the target low-molecular weight nucleic acid. Typically, the two layers are of different materials, although it is envisioned that the two layers can be the same material. Further, pore size between layers is typically different, with the larger pore size material on top of the smaller pore size material. Finally, additional capture matrix material layers may be added, although clogging of the filter material may become a greater concern.

Note that a frit may be included in the NA capture matrix, below the one or more capture matrix material layers for support. A typical frit is composed of an inert material, for example polyethylene, having a pore size of between 5 to 70 µm.

In an alternative embodiment, a portion, for example 350 µl of NA capture matrix slurry, e.g., a silica bead in solution, is deposited directly into the lysis solution/host cell material and incubated for a short period of time (typically with vortexing or other mixing technique). The capture matrix slurry/lysis solution mixture is spun down as above, and the pelleted matrix washed with an appropriate wash buffer. As above, the captured low molecular weight nucleic acid is released in an appropriate elution buffer. In addition, silica coated magnetized beads can be utilized as the NA capture matrix. The use and preparation of these beads is described in U.S. Pat. No. 6,368,800, which is incorporated herein by reference. Use of the silica coated magnetized beads obviates the need for centrifugation steps during the purification of target nucleic acid.

Table 2 provides illustrative NA capture matrix materials with corresponding pore sizes as well as several commercially available spin devices.

TABLE 2

NA Capture Matrix Materials

| NA Capture Matrix | Source |
|---|---|
| Glass Fiber | Ahlstrom 141, 142 |
|  | Whatman GF/C, GF/D |
| Nylon | Pall Biodyne |

Automation of Lysis Method

The methods and compositions of the present invention are useful in the isolation of high-yield and high-quality low molecular weight nucleic acid from target host cells during high throughput applications.

The methods of the present invention can be performed on one sample at a time using standard laboratory equipment and personnel. However, due to the limited number of steps/compositions required to perform the methods of the present invention, and due to the limited level of complexity of those steps, it is envisioned that the methods be utilized in a highly automated procedure for isolating target nucleic acid samples from a plurality of discretely handled samples.

In particular, the compositions and methods of the present invention can be used in a multi-well, for example 96 or 384 well, protocol. Cells are grown in the appropriate number of wells required for the particular procedure. After appropriate cell growth, the cells are pelleted using a multi-well plate centrifuge. Each cell sample in the multi-well plate is re-suspended in approximately 400 µl of pre-chilled lysis solution. Plates are shaken, or each wells constituents pipetted using a multi-channel pipette or 96-pin head, in order to re-suspend the cells completely. Samples are incubated for approximately 3 to 5 minutes at room temperature. Using the multi-channel pipette or 96-pin head, the lysate from each well is transferred to a corresponding multi-well filter plate. The lysate is vacuumed through the filter matrix (same types of capture matrix formats as discussed above) to capture the low-molecular weight nucleic acid on the capture matrix. Again using the multi-channel pipette or 96-pin head, approximately 400 µl of wash buffer is added to each well of the filter plate. Wash buffer is pulled over the capture matrix to remove residual protein and nucleic acid, and the vacuum is pulled until much of the residual alcohol is removed from the captured low-molecular weight nucleic acid. Appropriate plates are prepared for receiving the eluted low-molecular weight nucleic acid, and elution performed on each sample. This process of forcing liquids through the filter plate can also be performed using centrifugation. Note that centrifugation should be avoided during the automation process where the process is being performed on a automation workstation.

Finally, note that the automation procedures of the present invention can be performed using silica coated magnetized beads. The purification steps would be substantially the same as above, except that the NA capture matrix would be separated from the lysate using the magnetic properties of the beads and would not require a centrifugation step.

This process can be automated into a high-throughput procedure using pre-calibrated equipment. Other methods are envisioned for high-throughput operations and are not limited to 96-well or 384-well plates. As such, the methods of the present invention are ideal for the automated preparation of a large number of discrete high quality low molecular weight nucleic acid samples.

Low Molecular Weight Nucleic Acid Purification Kit

Embodiments of the present invention provide kits for the performance of the above described nucleic acid purification/isolation methods. In one embodiment of the present invention, the kit includes a lysis solution and NA capture matrix material (either as a spin column or matrix slurry). A preferred embodiment the kit further includes an elution solution and wash buffer. The kits of the present invention can also include molecular biology grade water, collection tubes, 384 well plates (optionally incorporating NA capture matrix), 96 well plates (optionally incorporating NA capture matrix), pipette tips, microcentrifuge, protective gloves, etc.

For maximum stability, the kits can contain lyophilized lysozyme, RNase and/or DNase that can be added to the lysis solution at the time of the kits first use. In some embodiments the detergent can also be provided separately for addition to the other ingredients just prior to use.

Finally, in some kits it is envisioned that a plurality of tubes used in the culture of cells, for example the Lid-Bac tube (U.S. Pat. Nos. 5,958,778 and 6,503,455, incorporated herein by reference), can also be included. These tubes would allow for the culture of target cells and the processing, lysis and solubilization of those same cells to be accomplished all in a single tube, using the lysis solution and methods of the present invention. The target nucleic acid is then isolated in that same tube by addition of a nucleic acid capture matrix slurry or in a second tube, for example a spin device having a layer of nucleic acid capture matrix directly incorporated therein.

Binding Solution

In an alternative embodiment in accordance with the present invention, a solution that includes a buffer, PEG, and salt is used to preferentially bind nucleic acid from a cleared lysate to a silica fiber. A preferred binding solution includes from 1 to 20% PEG having a molecular weight of from 2,000 to 10,000 daltons; from about 100 to 2000 mM salt, for example NaCl; from about 10 to 200 mM buffer, for example, Tris. NA capture matrix for use with this binding buffer includes silica beads and fibers. Preferred silica fibers have pores of from 1 to 20 µm, and more preferably from 3 to 5 µm.

Having generally described the invention, the same will be more readily understood by reference to the following examples, which are provided by way of illustration and are not intended as limiting.

EXAMPLES

Example 1

Preparation of Lysis Solution

Table 3 provides the composition of one potential lysis solution of the present invention. The concentration of each constituent is addressed for the amount of weight per liter of solution.

TABLE 3

Lysis Solution

| Ingredient | Concentration | Amount W or V per Liter |
|---|---|---|
| Polyethylene Glycol-8000 | 8.02% | 80.23 g |
| NaCl | 401 mM | 23.45 g |
| Tris Amino | 17.3 mM | 2.11 g |
| Tris Amino Hydrochloride | 28.5 mM | 4.47 g |
| 6.6M Guanidine Hydrochloride | 85.5 mM | 15.09 g |
| Guanidine Thiocyanate | 70.3 mM | 8.31 g |
| n-Decyl-N,N-dimethyl-3-ammonio-1-propanesulfonate | 3.05% | 30.55 g |
| 0.5M EDTA | 9.2 mM | 19.98 g |
| RNase A | 305 µg/ml | 305 mg |
| UF water | N/A | 870 g |
| 1N NaOH | N/A | as required |
| 1N HCl | N/A | as required |
| Egg White Lysozyme | 1000 µg/ml | 1000 mg |

Example 2

Room Temperature Incubation Increases Recovery of High Quality Plasmid DNA

The following Example illustrates that a three to ten minute room temperature incubation, and preferably a five minute room temperature incubation, of the lysis buffer on plasmid containing bacterial cells is beneficial for high yield recovery of high quality plasmid DNA.

Bacterial host cells were transformed with pUC19 plasmid and grown in 96 well plates overnight as is well known in the art. Plates were thawed for 15 minutes at room temperature, and approximately 400 µl of previously described Lysis buffer added per well of each plate. Note that the Lysis buffer was pre-chilled to 0° C. before addition to the bacterial cultures.

Cultures were then either immediately spun down, or re-suspended on a plate shaker, and incubated for a varying amounts of time at room temperature. Each lysate, having a varied 0 to 10 minute room temperature incubation, was removed and transferred to a silica based NA capture matrix and spun down at 14000 RPM for one minute. The resultant filtrate was removed from each well, and the NA capture matrix washed with a wash buffer solution (20 mM Tris-Cl pH 7.2, 0.2 M NaCl, 2 mM EDTA pH 8, 75% isopropanol). The wash buffer was spun off at 14000 RPM for one minute. Elution of the captured pUC19 from the NA capture matrix was performed using 50 µl elution buffer (10 mM Tris-Cl and 0.1 mM EDTA), and each elution sample tested for pUC19 yield and protein contamination.

Figure 1B:
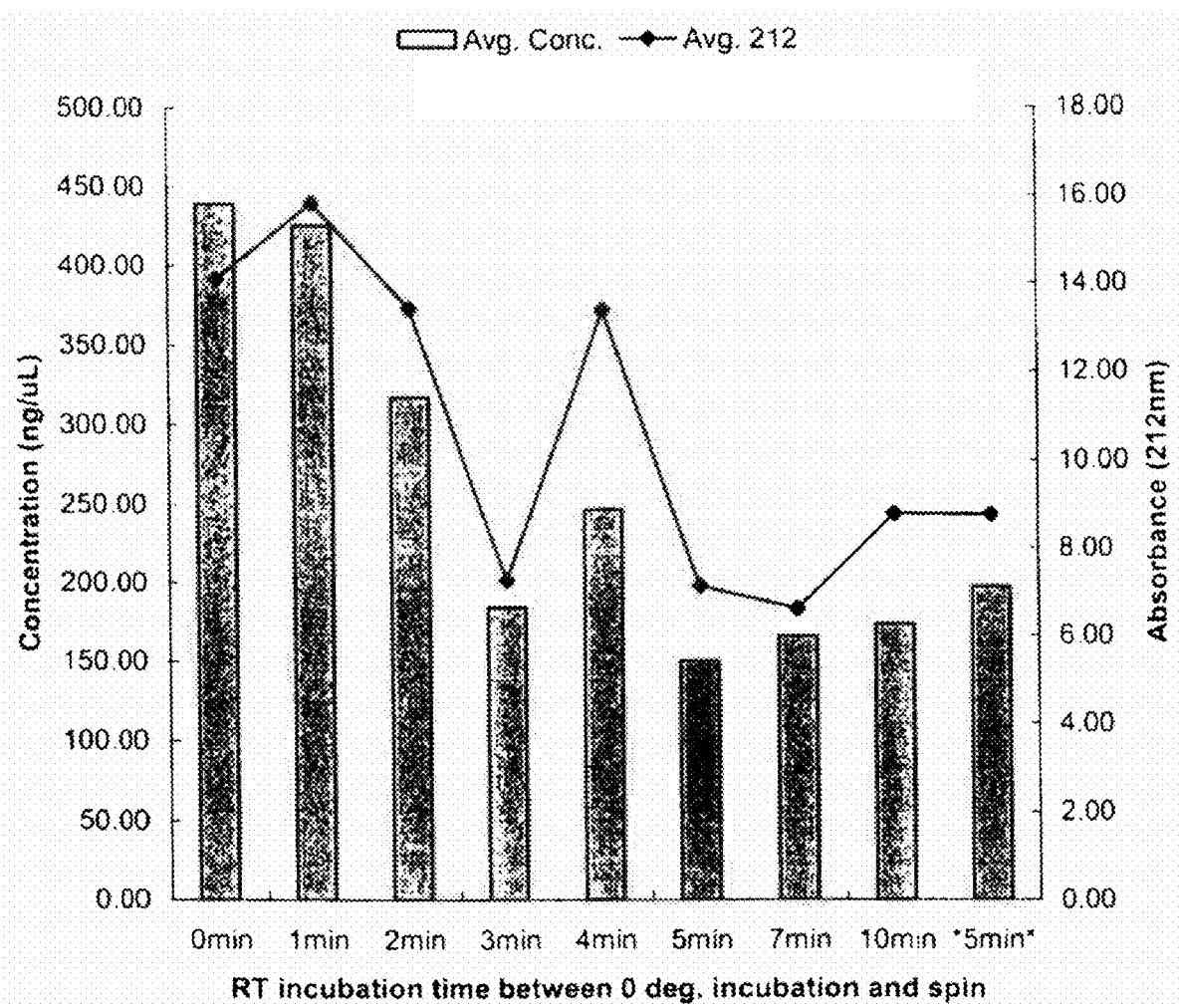

Referring to FIG. 1A, isolated plasmid DNA from each incubation condition was run on a 0.5% agarose gel. The ethidium bromide stained gel shows that all incubation conditions provided a good yield of plasmid DNA, including the immediate spin condition. FIG. 1B and Table 4 provide a graphical and tabular illustration of each sample's concentration and $A_{212}$ value in relation to the incubation time. Note that as room temperature incubation period proceed, the protein contamination in the sample decreased until about three minutes, at which time the protein and nucleic acid concentrations in the sample stabilize. Taken together, FIGS. 1A and 1B illustrate that a room temperature incubation of Lysis buffer on the target cells decreases the protein contamination of the isolated pUC19 while not adversely affecting the yield of the plasmid. This Example shows that a three to ten minute, and preferably a five minute, room temperature incubation of the Lysis on the host cells is useful for maximizing resultant low-molecular weight nucleic acid yield and purity. In addition, shorter incubations, zero to two minutes, appear to not fully allow for the contaminants to be separated from the target nucleic acid using the solutions and methods of the present invention. Note that the high concentration of DNA of short incubation times, as determined by absorbance readings, are inflated due to contamination and do not represent the actual concentrations. The concentrations shown for incubation times greater than or equal to three minutes are representative of the true concentration of the isolated DNA.

TABLE 4

Plasmid Yield and Protein Contamination With Varying Room Temperature Incubation

| R.T. Incubation | $A_{260/280}$ | Ave. Concentration[a] | Ave $A_{212}$ |
|---|---|---|---|
| Immediate spin | 1.86 | 440 | 14.12 |
| 1 min | 1.83 | 426.4 | 15.9 |
| 2 min | 1.84 | 318 | 13.4 |
| 3 min | 1.86 | 184.7 | 7.27 |
| 4 min | 1.75 | 247.7 | 13.4 |
| 5 min | 1.84 | 150.8 | 7.14 |
| 7 min | 1.87 | 166.3 | 6.6 |
| 10 min | 1.8 | 174.1 | 8.8 |

[a]Average concentration determined by spectroscopy. Absorbance readings for immediate spin, 1 minute, and 2 minute samples are inflated due to protein contamination as confirmed by visual inspection of sample DNA on stained agarose gel and via experiments performed to detect protein (not shown).

Example 3

Detergent Type and Concentration is Critical for Lysis Buffer Effectiveness

Methods and solutions used to transform bacterial host cells with nucleic acid as well as grow transformed cells for isolation of the nucleic acid are well known in the art. Further, the inventive methods used to purify the plasmid DNA from bacterial host cells are essentially the same as shown in Example 2 above, with the exception that the detergent type in the lysis buffer was varied to determine which types of detergents are most useful in the present context.

With regard to the lysis buffer conditions used in this Example, a standard lysis buffer was prepared having:
50 mM Tris-Cl (pH—8);
10 mM EDTA (pH—8);
350 µg/ml RNase;
1200 µg/ml Lysozyme;
7.5% PEG-8000;
1% detergent (type varied according to the sample);
50 µl/ml glass matrix beads; and
0.75 M NaCl.

Figure 2:
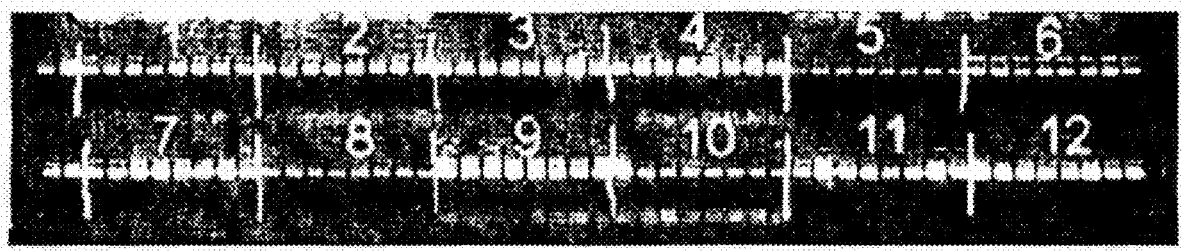
FIG. 2 illustrates plasmid DNA as visualized on a stained 0.5% agarose gel where the type of detergent used in the Lysis buffer has a dramatic effect on both the yield and quality of the purified plasmid DNA. The DNA was isolated on a glass fiber (second 1-12) plate.

A series of 12 different lysis buffers was prepared using this base composition above, each having a different type of detergent added to a final concentration of 1%. In particular, the detergents were (1) N,N',N'-Polyoxyethylene(10)—N-tallow-1,3-diaminopropaned (N,N,N-PTD), (2) NDSB-195, (3) NDSB-201, (4) NDSB-256, (5) Apo-10, (6) Apo-12, (7) CHAPS, (8) n-Octyl-B-D-glucopyranoside, (9) De-Oxcholic Acid, (10) SDS, (11) Triton X-100 mixed with SDS (50:50), and (12) Triton X-100. Note that the lysis buffer can be brought to a pH of 8.5 in the absence of the RNase, lysozyme and detergent. As shown in FIG. 2, the type of detergent used in the lysis buffer had a dramatic effect on both the yield and quality of the purified plasmid DNA. For example, the inclusion of N,N,N-PTD detergent resulted in a high yield/high quality one-step plasmid preparation, whereas under the exact same conditions, the inclusion of De-oxcholic Acid provided adequate yield of plasmid DNA, but lower quality purified plasmid DNA. As such, detergent type had a profound effect on resultant yield and quality.

A further series of experiments were performed using zwitterionic detergents to determine their effectiveness for use in the lysis buffer. In general, zwitterionic (zw) detergents were used at concentrations of between 1 to 4% to determine whether all or specific types of zwitterionic detergents are effective in the methods of the present invention. Interestingly, the zwitterionic detergents n-octyl-N,N-dimethyl-3-ammonio-1-propanesulfonate (zw-8), n-Decyl-N,N-dimethyl-3-ammonio-1-propanesulfonate (zw-10), n-Dodecyl-N,N-dimethyl-3-ammonio-1-propanesulfonate (zw-12) and n-Tetradecyl-N,N-dimethyl-3'-ammonio-1-propanesulfonate (zw-14) all showed either adequate (zw-8) or good results (zw-10, zw-12 and zw-14) (data not shown).

To further define the effectiveness of the zwitterionic detergents in lysis solutions, detergents were incorporated into the same lysis solution (zw-10, zw-12 and zw-14) alone, or in mixtures, at final concentrations that varied between 1% and 4%. Table 5 illustrates a summary of these results showing that zwitterionic detergents, present at from 1 to 4%, are excellent for high yield and purity isolation of low molecular weight nucleic acid from host cells. Data from lysis solutions using NP40 or Qiagen kit purified DNA were included for comparison.

TABLE 5

Zwitterionic Detergent Concentration And Type Effect Yield and Purity of Target Nucleic Acid

| Detergent Type | $A_{260/280}$ | Concentration ng/µl | $A_{212}$ |
|---|---|---|---|
| Varying ZW 3-12 and 3-14 From 1 to 4% | | | |
| 1% ZW 3-12 | 1.88 | 299.9 | 7.24 |
| 2% ZW 3-12 | 1.90 | 318.0 | 7.44 |
| 3% ZW 3-12 | 1.86 | 319.8 | 7.43 |
| 4% ZW 3-12 | 1.87 | 374.8 | 9.06 |
| 1% ZW 3-14 | 1.86 | 384.2 | 9.02 |
| 2% ZW 3-14 | 1.89 | 397.0 | 9.34 |
| 3% ZW 3-14 | 1.84 | 393.1 | 9.52 |
| 4% ZW 3-14 | 1.81 | 425.2 | 9.63 |
| 3% NP40 | 1.90 | 442.7 | 11.47 |
| Varying ZW 3-10 and 3-12 and Mixtures of Both From 2 to 3% | | | |
| 2% ZW 3-10 | 1.85 | 313.8 | 8.94 |
| 3% ZW 3-10 | 1.85 | 355.1 | 9.62 |
| 2% ZW 3-12 | 1.86 | 369.7 | 9.86 |
| 3% ZW 3-12 | 1.87 | 377.0 | 9.35 |
| 1.5% ZW 3-10/1.5% ZW 3-12 | 1.87 | 370.5 | 9.77 |
| 1.5% ZW 3-10/1.5% ZW 3-14 | 1.89 | 375.1 | 10.08 |
| 1.5% ZW 3-12/1.5% ZW 3-14 | 1.85 | 416.65 | 10.98 |
| 1% ZW 3-10/1% ZW 3-12/1% ZW 3-14 | 1.88 | 340.28 | 9.31 |
| Qiagen | 1.84 | 174.38 | 4.97 |

TABLE 5-continued

Zwitterionic Detergent Concentration And Type Effect Yield and Purity of Target Nucleic Acid

| Detergent Type | $A_{260/280}$ | Concentration ng/µl | $A_{212}$ |
|---|---|---|---|
| Varying Detergent Type With Temperature or Incubation Time | | | |
| 3% ZW 3-10/RT | 1.91 | 254.61 | 8.19 |
| 3% ZW 3-10/4° C. | 1.84 | 137.87 | 5.34 |
| 3% ZW 3-10/on ice | 1.82 | 110.7 | 4.44 |
| 3% ZW 3-12/RT | 1.99 | 455.58 | 13.24 |
| 3% ZW 3-12/4° C. | 1.99 | 319.47 | 9.15 |
| 3% ZW 3-12/on ice | 1.94 | 198.80 | 6.02 |
| 3% ZW 3-14/RT | 1.97 | 235.57 | 7.60 |
| 3% ZW 3-14/4° C. | 2.0 | 516.83 | 14.58 |
| 3% ZW 3-14/on ice | 1.94 | 198.80 | 6.02 |
| 3% ZW 3-10/2 minutes | 1.74 | 129.67 | 11.65 |
| 3% ZW 3-10/5 minutes | 1.84 | 127.86 | 5.20 |
| 3% ZW 3-12/2 minutes | 1.92 | 270.66 | 10.32 |
| 3% ZW 3-12/5 minutes | 1.95 | 171.93 | 5.33 |
| 3% ZW 3-14/2 minutes | 1.96 | 379.94 | 11.96 |
| 3% ZW 3-14/5 minutes | 1.89 | 217.09 | 7.67 |
| Qiagen control | 1.91 | 88.66 | 2.02 |

This data illustrates the effectiveness of using a zwitterionic detergent in the context of the lysis solutions and methods of the present invention.

Example 4

Pre-Chilled Lysis Solution Enhances Quality of Purified Nucleic Acid

The lysis methods and solutions of the present invention were used to evaluate the effect of adding different temperature lysis solutions to pUC19 transformed DH5α cells. The quality of the isolated pUC19 was determined as above.

Figure 3:
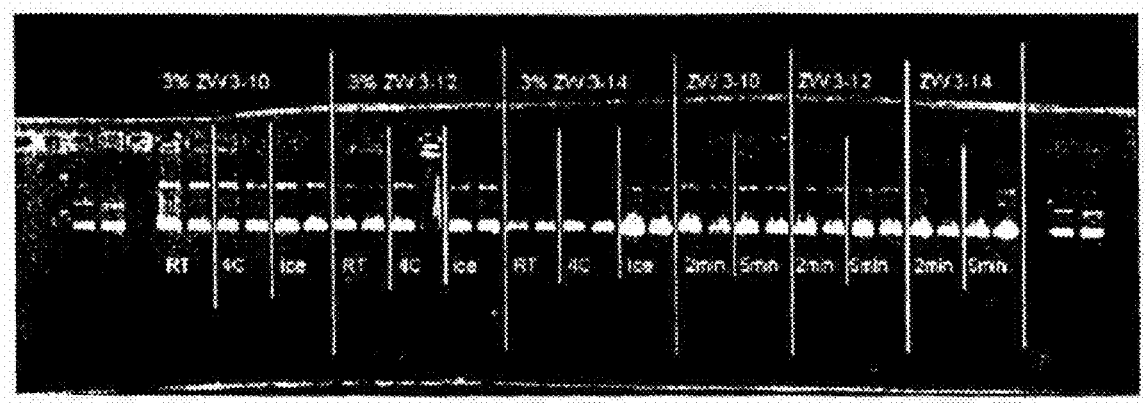
FIG. 3 illustrates plasmid DNA as visualized on a stained 0.5% agarose gel where the cells were incubated with room temperature Lysis solution, 4° C. Lysis solution, or 0° C. Lysis solution.

Methods and solutions used to transform cells with pUC19, and to grow transformed cells in anticipation of isolation of the pUC19 are well known in the art. Lysis solution as described in the Examples above was prepared having either a detergent composed of 3% zw 3-10, 3% zw 3-12, or 3% zw 3-14. Lysis solutions for each detergent condition were either left at room temperature, chilled to 4° C. or chilled to about 0° C. before addition to the cells. Results in Table 6 and FIG. 3 illustrate that the DNA isolated using the chilled lysis solutions (4° C. and 0° C.) provided higher quality isolated DNA than the DNA isolated using the lysis solution at room temperature. Lanes 3-18 in FIG. 3 show that the yield from each detergent type, at each temperature, was about the same (2 µl of each sample run per lane), conversely the absorbance readings from the same samples indicated that the isolated pUC19 using room temperature lysis solution, regardless of detergent type, had higher level of protein contaminants (see Table 6).

TABLE 6

Temperature of The Lysis Solution Effects NA Quality

| Sample Type | $A_{260}$ | $A_{280}$ | $A_{260/280}$ | Conc. ng/µl | $A_{212}$ |
|---|---|---|---|---|---|
| zw 3-10, RT | 0.255 | 0.133 | 1.91 | 254.6 | 8.19 |
| zw 3-10, 4° C. | 0.138 | 0.075 | 1.84 | 137.9 | 5.34 |
| zw 3-10, 0° C. | 0.111 | 0.061 | 1.82 | 110.8 | 4.44 |
| zw 3-12, RT | 0.456 | 0.229 | 1.99 | 455.6 | 13.2 |
| zw 3-12, 4° C. | 0.320 | 0.160 | 1.99 | 319.5 | 9.2 |
| zw 3-12, 0° C. | 0.199 | 0.103 | 1.94 | 198.8 | 6.0 |
| zw 3-14, RT | 0.236 | 0.119 | 1.97 | 235.6 | 7.6 |
| zw 3-14, 4° C. | 0.517 | 0.259 | 1.99 | 516.8 | 14.5 |
| zw 3-14, 0° C. | 0.205 | 0.102 | 2.1 | 204.5 | 6.1 |

This data generally illustrates that pre-chilled lysis solution provides for higher quality isolated plasmid DNA as compared to identical lysis solutions added to the cells at room temperature. Note, however, that lysis solution added to the cells at room temperature did provide isolated plasmid DNA, and that the isolated plasmid DNA was of a reasonably good quality.

Example 5

Matrix Material and Pore Size of Nucleic Acid Capture Matrix is Critical for High Yield and Quality Isolation The lysis methods of the present invention were used to evaluate a number of filter membrane substances, having different compositions and pore sizes, for effectiveness in isolating high quality low molecular weight nucleic acid. Both filter type and pore size were investigated for effectiveness at isolating high yield and high quality low-molecular weight nucleic acid.

The procedure for releasing the low molecular weight nucleic acid from target host cells was as described above. Briefly, target low molecular weight nucleic acid was propagated in target host cells in 96-well culture plates. Host cells were grown to a predetermined concentration, and cells spun down and growth media removed. Approximately 240 µl of pre-chilled lysis solution was added to each well and the cells re-suspended on a plate shaker for two minutes at a seven setting.

Filter conditions were varied in wells of filter plates, where wells in each plate had one of six filter combinations, which were prepared as follows: Sample 1 included a two layer NA capture matrix: layer one (top) was a glass fiber layer (1.2 µm pore size), layer two (middle) was a glass fiber (0.8 µm) and the frit was polyethylene; sample 2 included the same combination as sample one except the frit was hydrophobic; sample 3 included two layers, a first layer of 23 µm glass fiber filter on top of a frit having a pore size of 25 µm; sample 4 included a 11 µm glass fiber filter/polypropylene 25-30 µm combination; sample 5 included a 20 µm/11 µm glass fiber filters on a polypropylene 25-30 µm combination and sample 6 included a 7 µm glass fiber filter on a polypropylene 25-30 µm combination.

The results in Table 7 illustrate that, unlike conventional isolation techniques, the present invention provides optimal results with capture matrix having pore sizes that are generally greater than about 1 µm. Best results in the present Example were seen using the matrix combinations in samples 3 and 5, indicating that a 20 µm glass fiber filter over 11 µm glass fiber filter and a 23 µm glass fiber filter provided good low molecular weight nucleic acid capture and release characteristics for use in the present invention.

TABLE 7

NA Capture Matrix Results

| Sample | $A_{260/280}$ | Concentration ng/ml | $A_{212}$ |
|---|---|---|---|
| 1 | 1.45 | 370.7 | 36.6 |
| 2 | 1.36 | 4.89 | 0.31 |
| 3 | 1.88 | 290.9 | 11.0 |
| 4 | 1.48 | 426.9 | 46.7 |
| 5 | 1.88 | 879.9 | 32.2 |
| 6 | 1.78 | 213.2 | 9.4 |

A second series of experiments were performed using XL1 Blue/pUC19 grown in 1.5 ml host cell cultures and 400 µl lysis pre-chilled solution. Samples were incubated with lysis at room temperature for 5 minutes. Fourteen different capture matrix combinations were tested as follows: (1) Pallflex U100z Med. (rough side-up); (2) S&S GF#25; (3) Pall flex 2500-S2608G (smooth side-up); (4) Pallflex 2500-S2608G (rough side-up); (5) Pallflex 2500 AE 53009M (smooth side-up); (6) Pallflex 2500 AE 53009M (rough side-up); (7) Whatman GMF 934AH; (8) Whatman GMF 150 2 µm (two layers of same pore size); (9) Whatman 150 2 µm (top layer only); (10) 20 µm PE frit with a 5 µm GF layer; (11) one layer of 5 µm GF; (12) S&S GF number 24 (smooth side-up); (13) 23 µm glass fiber filter (Ciro) and (14) 23 µm glass fiber filter (Ciro) with a standard buffer.

Resultant isolated plasmid DNA was tested for concentration and quality as well as for use in sequencing reactions. (see Tables 8 and 9). Results indicate that glass fiber and larger pore size samples are good candidates for nucleic acid capture matrix.

TABLE 8

NA Capture Matrix Concentration, $A_{260/280}$, and $A_{212}$ Results

| Sample | $A_{260/280}$ | Concentration ng/ml | $A_{212}$ |
|---|---|---|---|
| 1 | 1.69 | 60.3 | 6.14 |
| 2 | 1.97 | 76.8 | 2.94 |
| 3 | 1.76 | 71.3 | 3.40 |
| 4 | 1.70 | 63.23 | 2.8 |
| 5 | 1.75 | 75.4 | 2.93 |
| 6 | 1.81 | 83.55 | 3.4 |
| 7 | 1.81 | 234.5 | 10.88 |
| 8 | 1.83 | 174.4 | 6.0 |
| 9 | 1.64 | 125.2 | 4.3 |

TABLE 9

Sequencing Quality Of Isolated Low Molecular Weight Nucleic Acid

| Sample | Mean | Std. Dev. | Std. Error | Count | Min. | Max. |
|---|---|---|---|---|---|---|
| 1 | 582.57 | 38.46 | 14.54 | 7 | 530 | 624 |
| 2 | 588.71 | 30.86 | 11.67 | 7 | 554 | 628 |
| 3 | 603.57 | 38.07 | 14.39 | 7 | 553 | 647 |
| 4 | 632 | 22.48 | 9.2 | 6 | 594 | 663 |
| 5 | 591.6 | 30.16 | 13.49 | 5 | 571 | 645 |
| 6 | 607.1 | 18.24 | 6.90 | 7 | 581 | 631 |
| 7 | 544.1 | 86.76 | 32.79 | 7 | 372 | 620 |
| 8 | 649.14 | 12.95 | 4.90 | 7 | 627 | 662 |
| 9 | 580.17 | 124.7 | 50.9 | 6 | 333 | 659 |
| 10 | 642.83 | 44.89 | 18.33 | 6 | 591 | 691 |
| 11 | 616.17 | 72.93 | 29.77 | 6 | 531 | 686 |
| 12 | 596 | 56.19 | 22.94 | 6 | 529 | 686 |

TABLE 9-continued

Sequencing Quality Of Isolated Low Molecular Weight Nucleic Acid

| Sample | Mean | Std. Dev. | Std. Error | Count | Min. | Max. |
|---|---|---|---|---|---|---|
| 13 | Not Tested | | | | | |
| 14 | Not Tested | | | | | |

Figure 4:
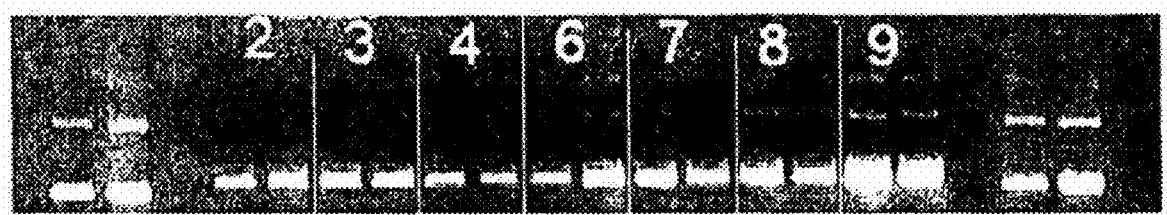
FIG. 4 illustrates that the type of NA capture matrix material and the pore size of that matrix have an effect on both yield and quality of the purified plasmid DNA. Isolated plasmid DNA was visualized on a stained 0.5% agarose gel.

A third series of experiments is shown in Table 10 and FIG. 4 where both NA capture matrix material and pore size were tested for capacity for isolating plasmid DNA from a bacterial host cell source. Bacterial host cells harboring XL1Blue/pBS2 were harvested and treated with lysis solution as previously described in the Examples above. Similarly treated samples were contacted to either a nylon, PVDF or glass fiber filter having pore sizes as described: (1) 0.45 μm Nylon fiber, (2) 1.2 μm Nylon fiber, (3) 5.0 μm Nylon fiber, (4) Pallflex® Emfab filter with 70 μm frit, (5) 0.45 μm PVDF, (6) 1.0 μm Glass fiber filter, (7) two layers of 1.2 μm glass fiber filters, (8) 23 μm glass fiber filter. (9) 5 μm glass fiber filter over a 3 μm glass fiber filter over a 20 μm frit.

FIG. 4 indicates that although isolation of the plasmid DNA using either nylon or Pallflex yielded adequate results, the glass fiber material, and in particular the two layers of glass fiber material in sample 9 provided for an excellent NA capture matrix in the context of the present invention. As shown in Table 10, the quality of the isolated plasmid DNA showed good $A_{260}/A_{280}$ ratios and $A_{212}$ readings, especially with regard to sample 9—the two layer glass fiber capture matrix having a first layer with a pore size of 5 μm and the second layer having a pore size of 3 μm.

TABLE 10

Plasmid DNA Quality

| Sample Number | $A_{260}/A_{280}$ | Concentration μg/ml | $A_{212}$ |
|---|---|---|---|
| 1 | N/A - clogged | | |
| 2 | 1.67 | 42.5 | 2.45 |
| 3 | 1.76 | 51.8 | 4.21 |
| 4 | 1.68 | 21.6 | 2.0 |
| 5 | N/A - clogged | | |
| 6 | 1.74 | 80.7 | 4.56 |
| 7 | 1.72 | 90.8 | 5.3 |
| 8 | 1.71 | 88.4 | 3.6 |
| 9 | 1.83 | 202.0 | 8.0 |

Example 6

Figure 5:
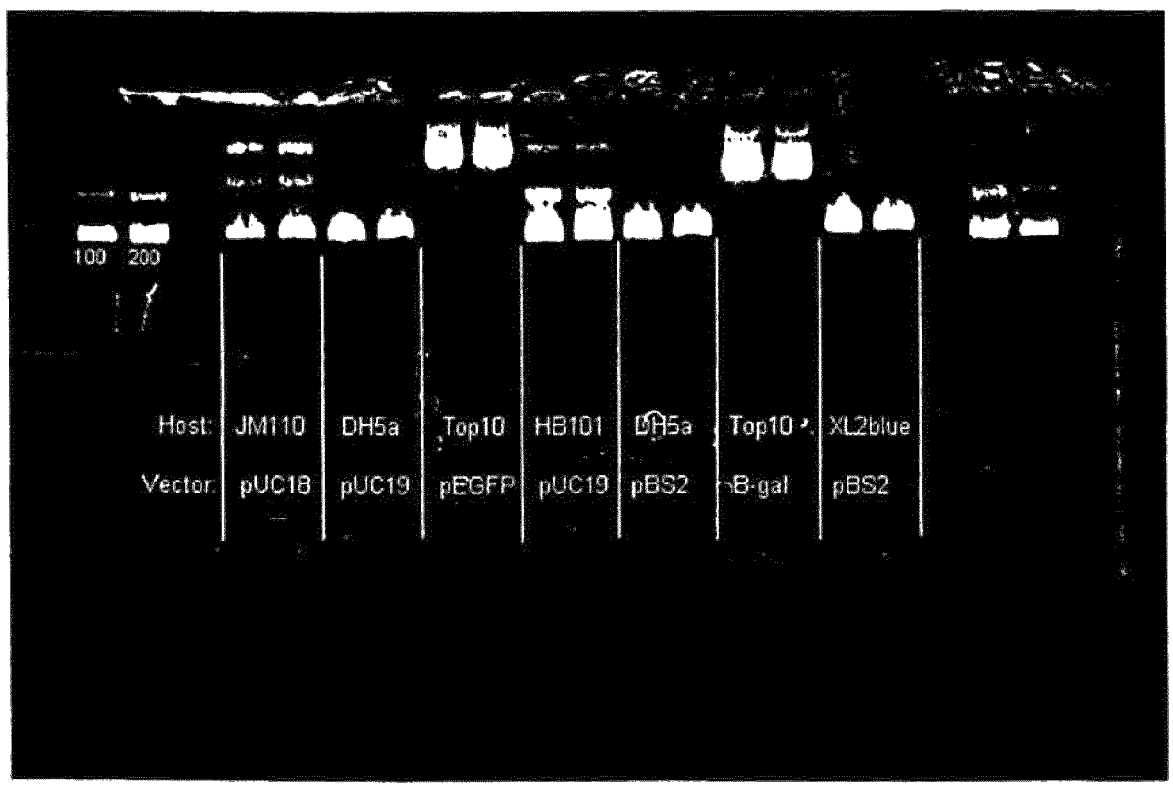
FIG. 5 illustrates that the methods and Lysis lysis solution of the present invention is useful in isolating different plasmid vectors from different types of host cells. Plasmid DNA samples were visualized on a stained 0.5% agarose gel.

Methods and Compositions of the Present Invention are Useful with a Number of Different Host Cells and Target Low Molecular Weight Nucleic Acids The data in the following Example illustrates that the lysis solutions are useful for the isolation of different sized plasmid DNA from several different host cells. Host cell/vector combinations were grown in LB/amp media overnight for 14 to 16 hours. Each cell condition consisted of 1.5 ml of pelleted culture, which was processed with 400 μl lysis solution (see Example 1). Data shown in Table 11 and FIG. 5, illustrate that the present methods and compositions are useful with a number of different host cells and different plasmids.

TABLE 11

Plasmid DNA From Different Host Cells

| Host Cell/Vector | $A_{260/280}$ | Concentration ng/ul | $A_{212}$ | Ave PHRED Q20 |
|---|---|---|---|---|
| JM110/pUC18 | 1.83 | 69.3 | 4.1 | 567 |
| DH5α/pUC19 | 1.92 | 150.8 | 6.2 | 524 |
| Top10/pEGLYSIS | 1.88 | 247.2 | 6.9 | NA |
| HB101/pUC19 | 1.86 | 133.1 | 5.7 | 516 |
| DH5α/pBS2 | 1.86 | 122.9 | 5.4 | 552 |
| Top10/β-gal | 1.88 | 394.3 | 10.4 | 588 |
| XL2blue/pBS2 | 1.87 | 164 | 6.4 | 586 |
| Top10/β-gal (Qiagen prep) | NA | NA | NA | 584 |

Example 7

Purified Low Molecular Weight Nucleic Acid can be Used Directly in PCR Reactions Purified low molecular weight nucleic acid may be directly amplified in a PCR reaction after recovery from the host cell using the methods and compositions of the present invention. Bacterial cells having a pGEM clone from a mouse cDNA library were treated using the methods and solutions of the present invention, and isolated pGEM was used directly in a PCR reaction, i.e., no additional steps performed on the pGEM after its elution off of the NA capture matrix of the present invention. The PCR reaction incorporated a T7 and a Sp6 primer and was performed using PCR methods well known in the art.

Figure 6:
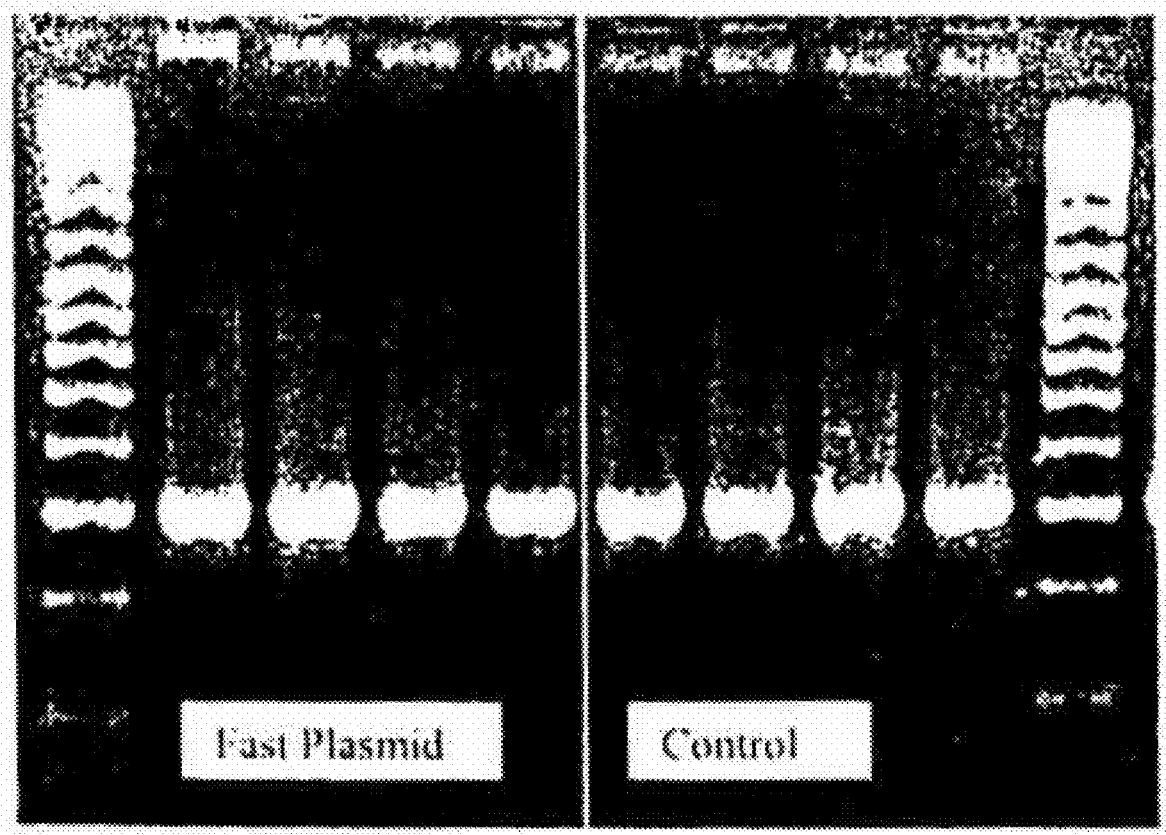
FIG. 6 illustrates that the plasmid DNA isolated via the methods and Lysis lysis solution of the present invention provide adequate template DNA for PCR. PCR products were visualized on a stained agarose gel.

As shown in FIG. 6, the pGEM DNA isolated using the methods and compositions of the present invention was an excellent template for PCR. This data indicates that the present invention provides quality DNA that can be directly used in PCR, importantly, the DNA does not require additional manipulation for its use in these reactions.

Example 8

Plasmid DNA can be Isolated in a 96-Well Format Using the Methods and Compositions of the Present Invention Bacterial host cells having a pUC19 plasmid were grown in 96-well plates to determine whether the methods and compositions of the present invention are applicable to high throughput applications.

Cells were grown and spun-down as described above, except that cells were grown in the wells of a 96 well plate and pelleted using a plate centrifuge. Approximately 400 μl of pre-chilled lysis solution was added to each well. Plates were either shaken, vortexed or each well individually pipetted up and down to thoroughly mix the cells in the lysis solution. A five minute room temperature incubation followed and the DNA eluted and analyzed. As shown in Table 12, plasmid DNA isolated from host cells grown in 96 well plates showed good quality and yield. Note that the plasmid DNA was captured in 96 well filter plates where each well has a pair of glass fiber layers having 5 μm and 3 μm pore sizes, the NA capture matrix on a 7 μm frit.

The data in this Example illustrates that the methods and compositions of the present invention are adaptable to high throughput applications, for example, 96-well format plates. Further the data indicates that mixing the cells with lysis solution can be accomplished by shaking the plates on a plate shaker, vortexing the plates on a plate vortex or pipetting the contents of each well using a 96 well pin.

TABLE 12

Data From 48 Wells of a 96 Well Plate

| Well Number | $A_{260}/A_{280}$ | Concen. µg/ml | $A_{212}$ | Mixing Step |
|---|---|---|---|---|
| A7 | 1.8 | 331.9 | 16.2 | Shaken |
| B7 | 1.8 | 302.5 | 14.6 | s |
| C7 | 1.8 | 284.0 | 13.5 | s |
| D7 | 1.8 | 252.2 | 12.3 | s |
| E7 | 1.8 | 252.2 | 11.8 | s |
| F7 | 1.8 | 294.1 | 14.0 | s |
| G7 | 1.8 | 249.2 | 11.3 | s |
| H7 | 1.8 | 248.7 | 11.1 | s |
| A8 | 1.8 | 351.6 | 17.1 | Shaken |
| B8 | 1.8 | 294.4 | 14.2 | s |
| C8 | 1.8 | 301.2 | 13.8 | s |
| D8 | 1.8 | 281.4 | 14.5 | s |
| E8 | 1.8 | 269.4 | 12.4 | s |
| F8 | 1.8 | 267.9 | 13.2 | s |
| G8 | 1.8 | 262.0 | 12.1 | s |
| H8 | 1.8 | 292.5 | 12.3 | s |
| A9 | 1.8 | 257.7 | 11.4 | Vortex |
| B9 | 1.8 | 249.7 | 11.5 | v |
| C9 | 1.8 | 275.2 | 12.7 | v |
| D9 | 1.8 | 259.3 | 12.8 | v |
| E9 | 1.8 | 277.8 | 13.0 | v |
| F9 | 1.8 | 276.8 | 13.5 | v |
| G9 | 1.8 | 239.7 | 11.8 | v |
| H9 | 1.8 | 281.4 | 12.3 | v |
| A10 | 1.8 | 252.8 | 11.8 | Vortex |
| B10 | 1.8 | 241.4 | 11.4 | v |
| C10 | 1.8 | 226.7 | 10.7 | v |
| D10 | 1.8 | 223.6 | 12.0 | v |
| E10 | 1.8 | 248.8 | 14.5 | v |
| F10 | 1.8 | 270.2 | 15.5 | v |
| G10 | 1.8 | 261.6 | 15.3 | v |
| H10 | 1.8 | 286.9 | 14.0 | v |
| A11 | 1.8 | 209.1 | 13 | Pipette |
| B11 | 1.8 | 187.4 | 10.2 | p |
| C11 | 1.8 | 239.2 | 14.6 | p |
| D11 | 1.8 | 277.1 | 28.2 | p |
| E11 | 1.8 | 261.2 | 24.0 | p |
| F11 | 1.8 | 299.1 | 30 | p |
| G11 | 1.8 | 284.9 | 27.3 | p |
| H11 | 1.8 | 342.0 | 38.2 | p |
| A12 | 1.8 | 234.1 | 14.6 | Pipette |
| B12 | 1.8 | 225.0 | 13.4 | p |
| C12 | 1.8 | 222.5 | 14.4 | p |
| D12 | 1.8 | 301.3 | 28.0 | p |
| E12 | 1.8 | 307.9 | 32.6 | p |
| F12 | 1.7 | 343.1 | 42.0 | p |
| G12 | 1.7 | 314.6 | 40.3 | p |
| H12 | 1.7 | 313.7 | 40.6 | p |

Example 9

Quality of Plasmid DNA Purified Using the Methods and Compositions of the Present Invention are Comparable to Other Conventional Plasmid DNA Purification Methods Two to five milliliters of culture (Top10 cells/pSV-β-gal) from a streak LB agar plate were grown overnight to reach a desired cell density. Growth was performed in 15 ml conical tubes. Approximately 1.5 mls of cells was harvested and pelleted and processed according to either the methods and compositions as described in the present invention (see Examples 1-8) or to manufactures suggestions (Qiagen, Invitrogen, BioRad, or Promega). In particular, the quality of the plasmid DNA isolated using the lysis solution were compared to plasmid DNA isolated using QIAprep Miniprep kit, Wizard® Plus SV Minipreps DNA purification system (Promega), Aurum® Plasmid Mini Kit (BioRad), S.N.A.P. MiniPrep Kit (Invitrogen). Similar numbers of starting cells and elution volumes were used for each method.

Purified Plasmid DNA was compared via agarose gel analysis, spectrophotometric analysis, DNA sequencing and restriction enzyme digestion.

Figure 7A:
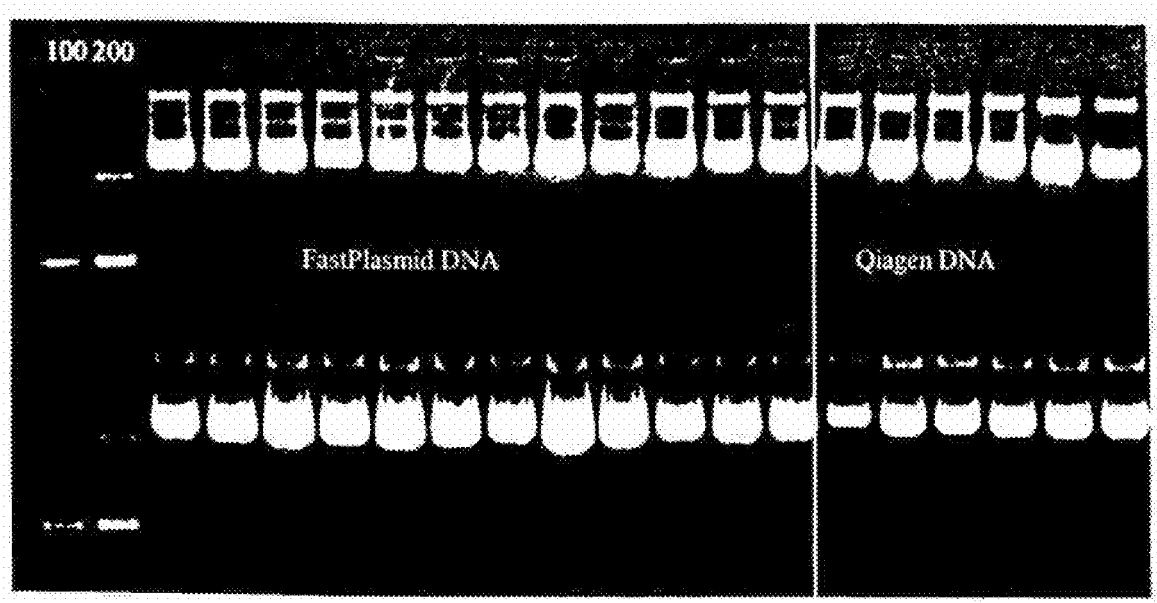
FIGS. 7A and 7B illustrate that the Lysis lysis method provides excellent concentrations and yields, comparable or better, to the QIAgen, Invitrogen, BioRad or Promega kits via a spectrophotometric analysis.

Agarose Gel Analysis: Approximately 4% of the plasmid DNA isolated using the QIAgen methods and the lysis methods described herein were loaded onto a 1% agarose gel containing ethidium bromide. Note that 1.5× Orange II dye was added to each sample prior to loading on the gel. In addition, 100 ng and 200 ng of pUC19 plasmid DNA was loaded as control DNA. As shown in FIG. 7A, plasmid DNA isolated according to the present methods provided comparable yields as QIAgen isolated plasmid DNA.

Figure 7B:
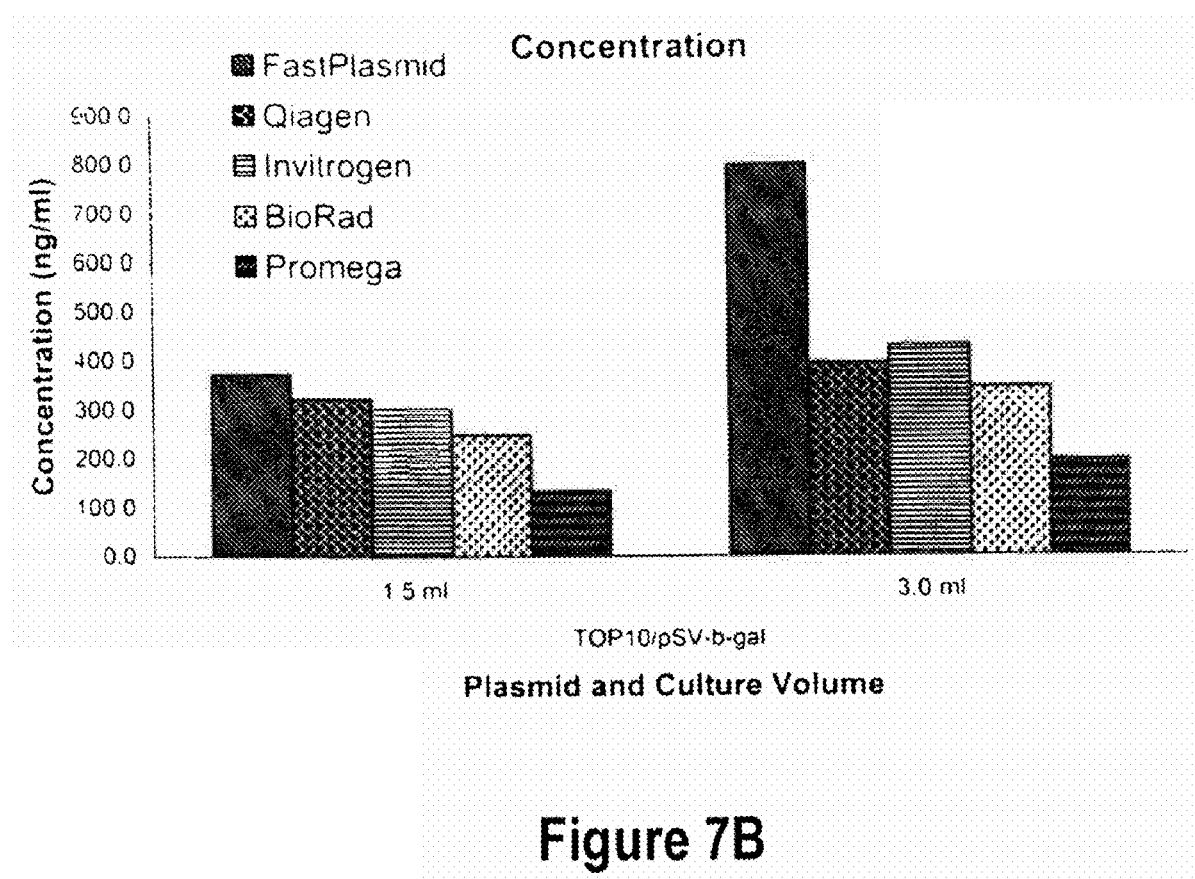

Spectrophotometric Analysis Samples from each of the purification methods were analyzed using a SPECTRAmax Microplate Spectrophotometer (Molecular Devices Corp.) to determine DNA concentration and purity. Samples were diluted 20 fold in a UV-Star 96 well plate (Greiner bio-one Corp.). Absorbance readings were taken at the following wavelengths, 260, 280, and 212 nm. Each sample was run in duplicate. Concentration and $A_{260/280}$ ratios were averaged to determine values presented in FIG. 7B. The data in FIG. 7B illustrates that the instant lysis method provides excellent concentrations and yields, comparable or better, to the QIAgen, Invitrogen, BioRad or Promega kits.

DNA Sequencing: Samples for each method were further analyzed by sequencing with ABI BigDye™ Terminator chemistry on the ABI 3700 sequencer. Sequencing was performed on the plasmid DNA and performed in duplicate. Template DNA was added to the reaction and varied according to vector and pelleted starting material. Between 200 ng and 300 ng of template DNA was aliquoted into a 96 well plate (Genemate-ISC Bioexpress) in a total volume of 4 µl. Sequencing parameters were as follows: step 1-94° C. for two minutes; step 2-94° C. for ten seconds; step 3-50° C. for five seconds; step 4-70° C. for four minutes; step 5—go to step two and repeat 25 times and step 6-10° C. hold.

Sequencing cleanup was performed prior to loading onto the ABI 3700 DNA sequencer. Approximately fifteen micro liters of 99% isopropanol was added to each well and heat sealed using Expender Heat Sealer and then vortexed briefly. Samples were incubated at room temperature for fifteen minutes and centrifuged at 1900×g for thirty minutes. Following centrifugation the heat seal was removed and the plate inverted on a paper towel and returned to the centrifuge plate carrier upside-down. The plate was spun at 500×g for one minute. The plate was removed and the centrifuge and DNA resuspended in ten micro liters of ¹⁄₁₀× TE and loaded onto the sequencer. Quality score was performed using PHRED based software version 0.020425.c (CodonCorporation). Passing results were determined to be those samples with 100 quality score ≧20.

Figure 8:
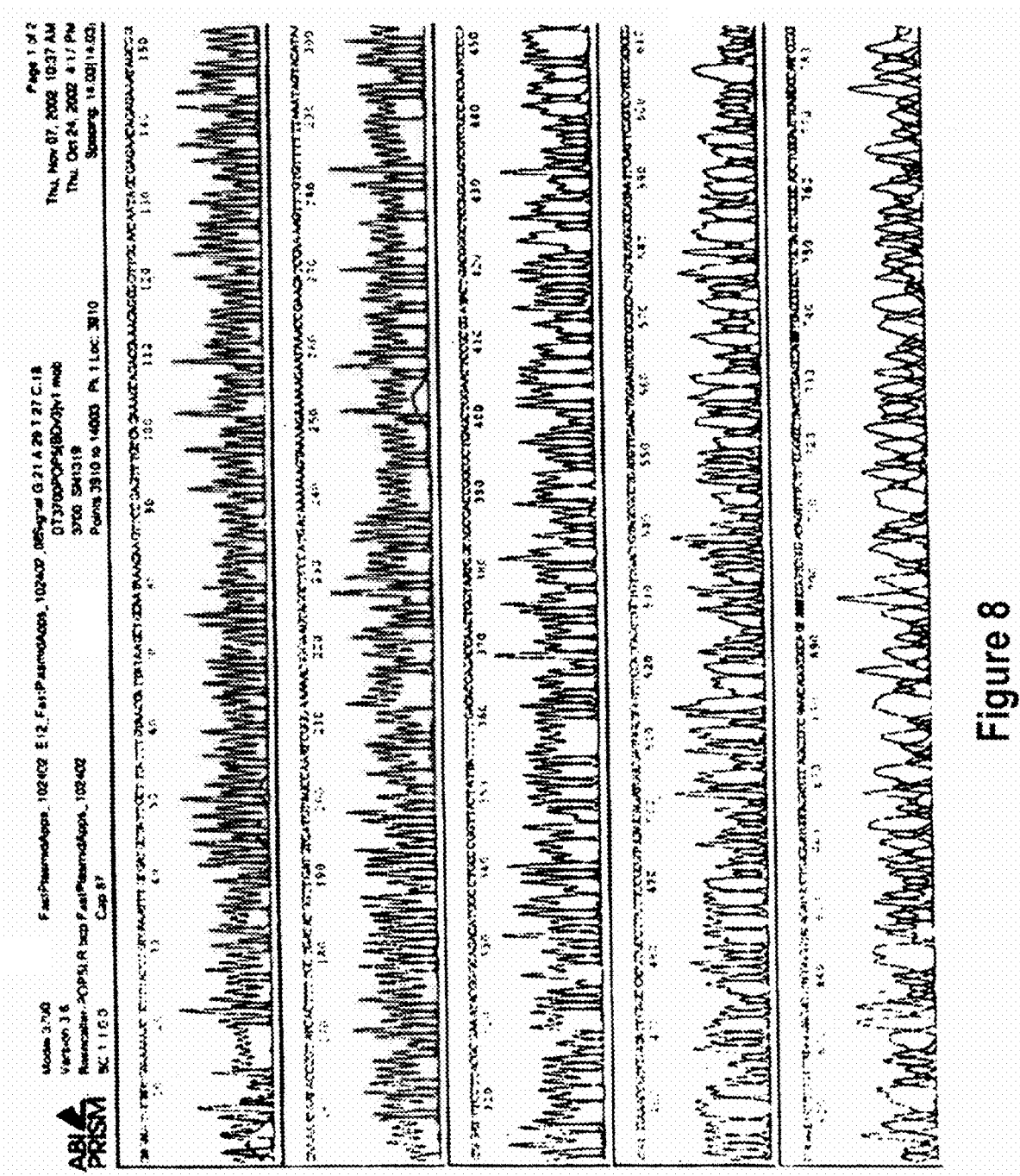
FIG. 8 illustrates the sequencing quality, via a sequencing trace, of DNA isolated using the methods and Lysis solutions of the present invention.

As shown in Table 13, all five kits provided passing sequencing scores. Further, FIG. 8 provides an illustrative sequencing trace for each kit's DNA. The data indicates that the instant lysis and purification methods and compositions provide comparable quality DNA to the DNA isolated using the other kit manufacturers. Note that the instant method, including elution steps, is performed in approximately 14 minutes, whereas QIAgen takes approximately 28 minutes, Invitrogen takes approximately 31 minutes, Promega takes approximately 36 minutes, and BioRad Aurum kit takes approximately 23 minutes. This data illustrates the improved utility of the lysis solutions and methods described herein.

TABLE 13

Passing Sequencing Scores
Passing Score
pSV-β-galactosidase

|  | 1.5 ml | | 3.0 ml | |
| --- | --- | --- | --- | --- |
| Lysis Compositions Of Present Invention | 6/6 | 100% | 3/6 | 50% |
| Qiagen | 6/6 | 100% | 5/6 | 83% |
| Promega | 2/2 | 100% | | |
| Invitrogen | 2/2 | 100% | | |
| BioRad | 2/2 | 100% | | |

Figure 9:
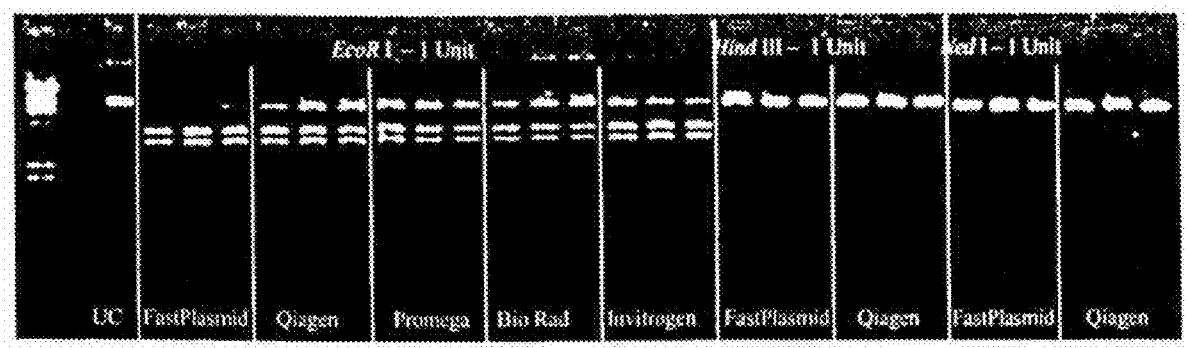
FIG. 9 illustrates the quality of DNA isolated using the methods and Lysis solutions of the present invention via a restriction endonuclease reaction as compared to other commonly used DNA isolation kits.

Restriction Enzyme Digestion: Restriction digestion was performed on the pSV-β-gal vector using EcoRI, Hind III and Ned I. Restriction digestions were performed on 250 ng of plasmid DNA and 1 unit of each endonuclease. Buffer conditions are as described by the enzyme manufacturer. As shown in FIG. 9, the lysis isolated DNA provided comparable template DNA for restriction endonuclease as did other conventional isolation methods.

Example 10

PEG and Salt Binding Solution Drives NA Binding to Silica Fibers

The data in the following Example illustrates that a solution of PEG and salt can be used to force binding of low molecular weight nucleic acid to a glass fiber based NA capture matrix. Host cells having pUC19 were treated using the alkaline lysis method, as is well known in the art. Cleared lysate was placed on the silica based spin devices of the present invention and yield and $A_{260/280}$ readings on the isolated pUC19 determined. Alternatively, cleared lysate was combined with a 8.5% PEG/850 mM NaCl solution and treated substantially the same as the cleared lysate above.

Figure 10A:
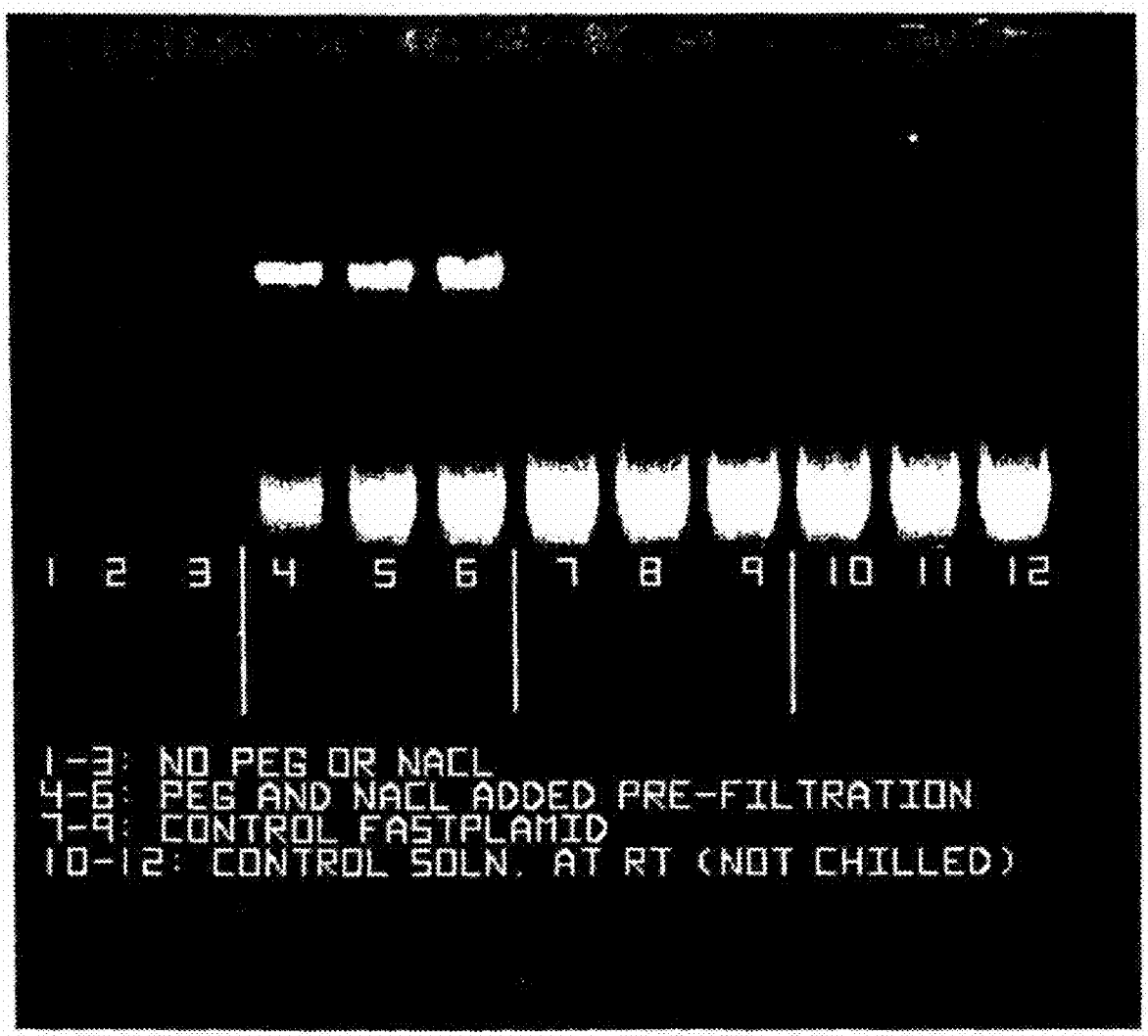
FIGS. 10A and B illustrate that a solution of PEG, salt and buffer can drive nucleic acid binding to silica particles. In A and B, the isolated plasmid DNA is visualized via a 0.5% agarose gel.
Figure 10B:
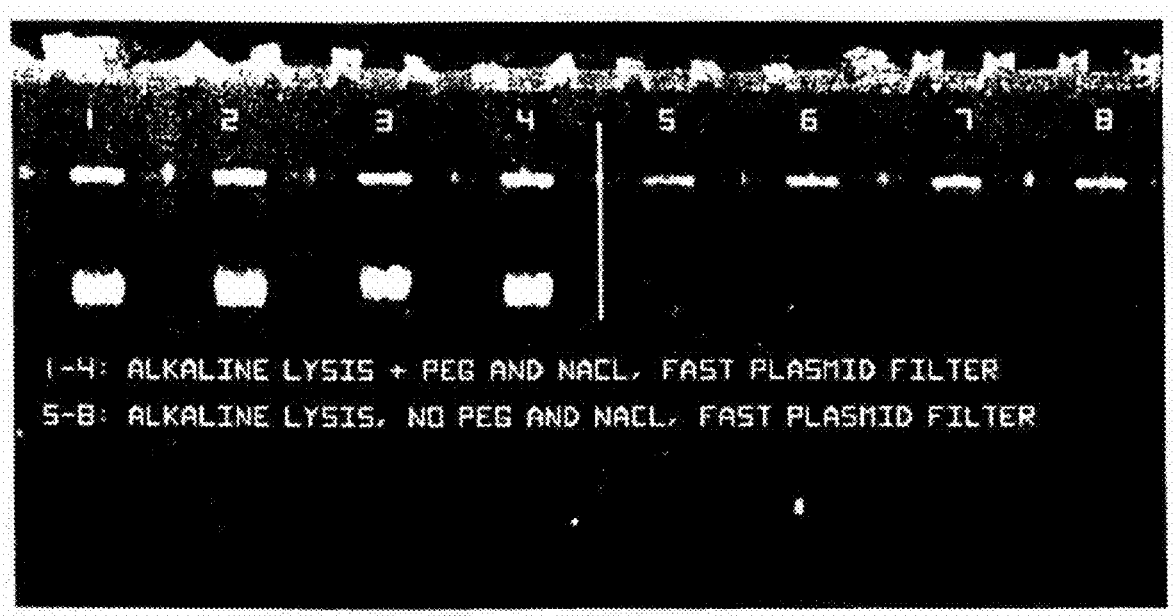

As indicated in FIG. 10B, PEG and salt drive binding of the pUC19 in the cleared lysate to silica based fiber (lanes 1-4). In comparison, cleared lysate having no PEG and salt added failed to provide any detectable pUC19 binding to target silica based capture matrix (lanes 5-8). As shown in FIG. 10A, the best results are obtained when the lysis solution of the present invention is used in conjunction with the NA capture matrix of the present invention—where the lysis solution includes both PEG and salt at the pre-described concentrations (as shown in lanes 4-6 and 7-9). Note that lanes 1-3 show no purification of plasmid DNA when the lysis solution of the present invention contains no PEG or salt.

Example 11

Lysis Solution can be Added Directly to Cell Culture During Nucleic Acid Purification Methods of Present Invention The data in the following Example illustrates that the lysis solution described herein is effective in the methods of the present invention even when added directly to a liquid bacterial culture (cells not pelleted). Lysis solution was prepared as described in Example 1. Samples were added to either a multi-layer glass fiber (5 μm and 3 μm) filter device or a single layer Whatman 23 μm glass fiber filter device.

Approximately 1.5 ml of pUC19/XL1blue transformed cell culture was mixed with 2.25 ml chilled lysis solution and cells vortexed for thirty seconds. Cells were allowed to incubate for 3 minutes at room temperature and approximately 930 μl of the lysate removed and added to either the multi-layer of single layer spin device for isolation of pUC19. Note that each culture was split into four samples, resulting in a yield that is ¼ of what would normally be expected from a 1.5 ml culture. Lysate was spun down in the spin devices and filters washed with approximately 500 μl wash buffer. Plasmid elution was performed as previously described. Absorbance readings and gel electrophoresis was performed as described above.

Figure 11:
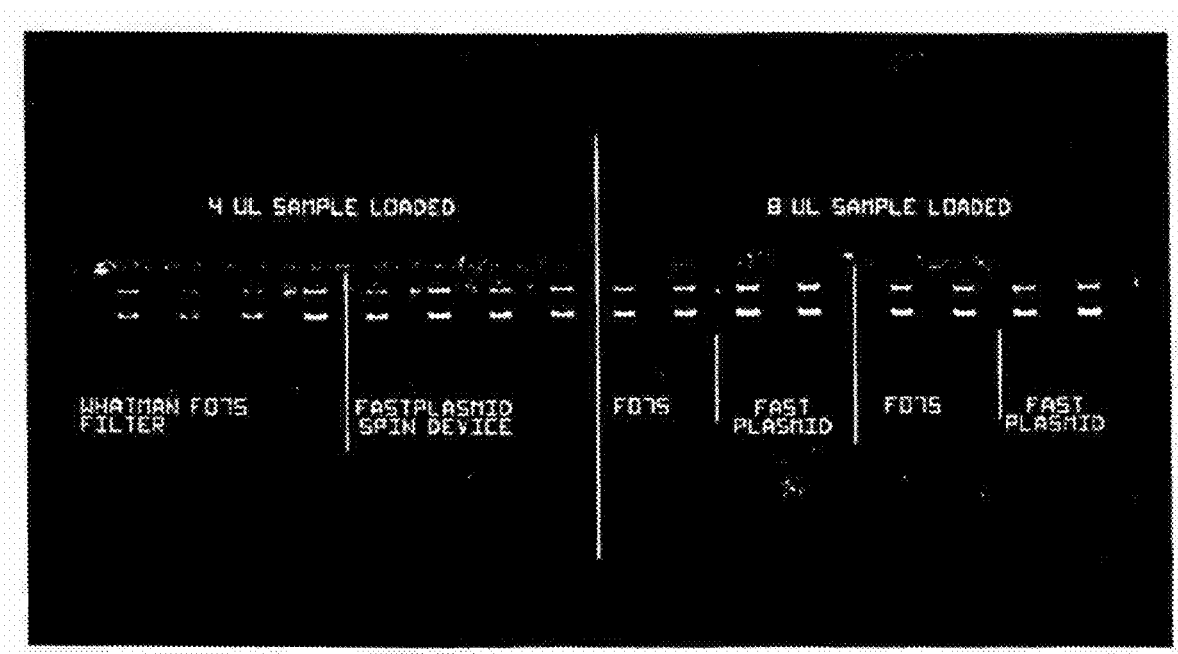
FIG. 11 illustrates that the Lysis solution can be added directly to a liquid bacterial culture and high quality plasmid DNA isolated using the methods and materials of the present invention. Isolated DNA samples were visualized on a stained agarose gel.

As shown in Table 14 and FIG. 11, the extraction of plasmid DNA directly from a liquid culture resulted in the extraction and purification of high quality DNA. Results showed little protein or RNA contamination (see $A_{260/280}$ readings and plasmid bands in FIG. 11). These results indicate that the methods and solutions of the present invention can be incorporated into a procedure that does not require the cells be pelleted before addition of the lysis solution. This is an impressive result—allowing the methods and solutions of the present invention to be used to further reduce the complexity and time required to isolate high quality nucleic acid from a target starting material.

TABLE 14

Data From Direct Mixing of Liquid Culture and Lysis Solution (All Readings Performed Twice)

| Filter Type | Sample # | $A_{260}$ | $A_{280}$ | $A_{260/280}$ | Conc. μg/ml | $A_{212}$ |
| --- | --- | --- | --- | --- | --- | --- |
| Single 23 μm glass fiber filter | 1 | 0.03/0.03 | 0.02/0.02 | 1.72/1.75 | 33/32.7 | 2.5/2.4 |
|  | 2 | 0.03/0.04 | 0.02/0.02 | 1.77/1.7 | 33/34.9 | 2.6/2.6 |
|  | 3 | 0.03/0.03 | 0.02/0.02 | 1.76/1.76 | 30.9/29.7 | 2.2/2.2 |
|  | 4 | 0.04/0.04 | 0.02/0.02 | 1.73/1.79 | 37.8/37.6 | 3.5/3.5 |
| Multiple: 5 and 3 μm glass fiber filter | 1 | 0.03/0.03 | 0.02/0.02 | 1.66/1.62 | 33.4/31.1 | 2.7/2.5 |
|  | 2 | 0.03/0.03 | 0.02/0.02 | 1.74/1.74 | 34.3/34.3 | 1.9/1.9 |
|  | 3 | 0.04/0.04 | 0.02/0.02 | 1.64/1.55 | 37.6/37.3 | 1.8/1.9 |
|  | 4 | 0.04/0.04 | 0.02/0.02 | 1.58/1.56 | 35.5/37.8 | 1.8/1.8 |

What is claimed is:

1. A method for separating intact low molecular weight nucleic acid from cellular protein during enzymatic lysis of a host cell, said method comprising:
    adding an enzymatic lysis solution including a zwitterionic detergent to said host cell to release at least a portion of said low molecular weight nucleic acid from the cellular proteins solubilized by the zwitterionic detergent;
    combining said host cell with a nucleic acid capture matrix, said nucleic acid capture matrix having at least one layer of capture matrix material for capture of at least a portion of said released low molecular weight nucleic acid wherein a step of separating the solubilized cellular proteins from the released low molecular weight nucleic acid is not required before contact of the host cell with the nucleic acid capture matrix; and
    eluting said low molecular weight nucleic acid from said nucleic acid capture matrix.

2. The method of claim 1, wherein said zwitterionic detergent in said lysis solution is at from about 0.2% to about 6% by weight.

3. The method of claim 2, wherein said zwitterionic detergent in said lysis solution is at from about 1% to about 5% by weight.

4. The method of claim 1, wherein said zwitterionic detergent in said lysis solution is selected from the group consisting of n-Octyl-N,N -dimethyl-3-ammonio-1-propanesulfonate, n-Decyl-N,N-dimethyl-3-ammonio-1-propanesulfonate, n -Dodecyl-N,N-dimethyl-3-ammonio-1-propanesulfonate, n-Tetradecyl-N,N-dimethyl-3-ammonio-1-propanesulfonate, n-Hexadecyl-N,N-dimethyl-3-ammonio-1-propanesulfonate, and mixtures thereof.

5. The method of claim 1, wherein said lysis solution further comprises polyethylene glycol.

6. The method of claim 5, wherein said polyethylene glycol is at a final concentration of from about 2% to about 20% by weight.

7. The method of claim 5, wherein said polyethylene glycol has a molecular weight of between about 2,000 and about 10,000 Daltons.

8. The method of claim 1, wherein said lysis solution further comprises lysozyme.

9. The method of claim 1, wherein said lysis solution further comprises RNase and/or DNase.

10. The method of claim 1, wherein said lysis solution further comprises a chaotropic salt.

11. The method of claim 1, wherein said lysis solution further comprises one or more of a salt, a chelating agent, and an alcohol.

12. The method of claim 1, wherein said nucleic acid capture matrix material for capture of said low molecular weight nucleic acid has an average pore size of at least about 1 μm.

13. The method of claim 1, wherein said nucleic acid capture matrix material for capture of said low molecular weight nucleic acid has an average pore size of at least about 3 μm.

14. The method of claim 1, wherein said nucleic acid capture matrix comprises at least two layers of capture matrix material having different pore sizes between said layers.

15. The method of claim 14, wherein a larger pore size material is on top of a smal pore size material in said nucleic acid capture matrix.

16. The method of claim 1, wherein said enzymatic lysis solution is chilled to a temperature below room temperature before addition to said host cell.

17. The method of claim 16, wherein said temperature is from about 0° C. to about 4° C.

18. The method of claim 17, further comprising: incubating said enzymatic lysis solution on said host cell at room temperature for at least about three minutes prior to combining with said nucleic acid capture matrix.

19. The method of claim 18, wherein said incubation is for at least five minutes.

20. A method for separating intact low molecular weight nucleic acid from cellular protein during enzymatic lysis of a host cell, said method comprising:
    adding an enzymatic lysis solution to said host cell to solubilize said cellular proteins and release at least a portion of said low molecular weight nucleic acid, wherein said enzymatic lysis solution consists essentially of a zwitterionic detergent; a polyethylene glycol; salt; lysozyme; RNase or DNase; and
    optionally, one or more of a chelating agent, a chaotropic salt, and an alcohol; in a buffered solution having a final pH from about 7.0 to about 8.4;
    combining said host cell with a nucleic acid capture matrix, said nucleic acid capture matrix having at least one layer of capture matrix material for capture of at least a portion of said released low molecular weight nucleic acid wherein a step of separating the solubilized cellular proteins from the released low molecular weight nucleic acid is not required before contact of the host cell with the nucleic acid capture matrix; and
    eluting said low molecular weight nucleic acid from said nucleic acid capture matrix.

21. A method for separating intact low molecular weight nucleic acid from cellular protein during enzymatic lysis of a host cell, said method comprising:
    adding a chilled enzymatic lysis solution including a zwitterionic detergent to said host cell to release at least a portion of said low molecular weight nucleic acid from the cellular proteins solubilized by the zwitterionic detergent; wherein said chilled enzymatic lysis solution is at a temperature below room temperature;
    incubating said enzymatic lysis solution on said host cell at room temperature;
    combining said host cell with a nucleic acid capture matrix, said nucleic acid capture matrix having at least one layer of capture matrix material for capture of at least a portion of said released low molecular weight nucleic acid wherein a step of separating the solubilized cellular proteins from the released low molecular weight nucleic acid is not required before contact of the host cell with the nucleic acid capture matrix; and
    eluting said low molecular weight nucleic acid from said nucleic acid capture matrix.

* * * * *